US008530629B2

(12) United States Patent
Chang

(10) Patent No.: US 8,530,629 B2
(45) Date of Patent: Sep. 10, 2013

(54) LOWERED AFFINITY ANTIBODIES AND USES THEREFOR

(75) Inventor: Hsiu-Ching Chang, Lexington, MA (US)

(73) Assignee: AB Biosciences, Inc., Allston, MA (US)

( * ) Notice: Subject to any disclaimer, the term of this patent is extended or adjusted under 35 U.S.C. 154(b) by 0 days.

(21) Appl. No.: 13/146,805

(22) PCT Filed: Jan. 29, 2010

(86) PCT No.: PCT/US2010/022592
§ 371 (c)(1),
(2), (4) Date: Jul. 28, 2011

(87) PCT Pub. No.: WO2010/088522
PCT Pub. Date: Aug. 5, 2010

(65) Prior Publication Data
US 2011/0287533 A1 Nov. 24, 2011

Related U.S. Application Data

(60) Provisional application No. 61/148,578, filed on Jan. 30, 2009.

(51) Int. Cl.
C07K 16/00 (2006.01)
C12P 21/08 (2006.01)

(52) U.S. Cl.
USPC .................................. 530/387.1; 530/388.75

(58) Field of Classification Search
None
See application file for complete search history.

(56) References Cited

U.S. PATENT DOCUMENTS

| | | | |
|---|---|---|---|
| 4,595,661 A | 6/1986 | Cragle et al. | |
| 4,816,567 A | 3/1989 | Cabilly et al. | |
| 4,873,316 A | 10/1989 | Meade et al. | |
| 5,225,539 A | 7/1993 | Winter | |
| 5,272,071 A | 12/1993 | Chappel | |
| 5,565,332 A | 10/1996 | Hoogenboom et al. | |
| 5,714,350 A | 2/1998 | Co et al. | |
| 5,733,743 A | 3/1998 | Johnson et al. | |
| 5,871,907 A | 2/1999 | Winter et al. | |
| 6,350,861 B1 | 2/2002 | Co et al. | |
| 2003/0108548 A1* | 6/2003 | Bluestone et al. | 424/144.1 |
| 2003/0219845 A1 | 11/2003 | Ruiz et al. | |
| 2008/0025979 A1* | 1/2008 | Honjo et al. | 424/136.1 |

FOREIGN PATENT DOCUMENTS

| | | |
|---|---|---|
| EP | 0171496 B1 | 5/1993 |
| EP | 0264166 B1 | 8/1996 |
| EP | 0125023 B2 | 3/2002 |
| WO | 8601533 A1 | 3/1986 |
| WO | 8702671 A1 | 5/1987 |
| WO | 9106667 A1 | 5/1991 |
| WO | 9945962 A1 | 9/1999 |
| WO | WO 2004072286 A1 * | 8/2004 |
| WO | 2010088522 A2 | 8/2010 |

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
Verhoeyen et al. (1988) "Reshaping Human Antibodies: Grafting an Antilysozyme Activity," Science 239:1534-1536.
Wada et al. (1992) "Codon Usage Tabulated From the GenBank Genetic Sequence Data," Nucleic Acids Res., 20 (Suppl):2111-2118.
Winoto et al. (1989) "A Novel, Inducible and T Cell-Specific Enhancer Located at the 3' End of the T Cell Receptor α Locus" EMBO J. 8(3):729-733.
Wood et al. (1985) "The Synthesis and In Vivo Assembly of Functional Antibodies in Yeast," Nature 314:446-449.
International Search Report and Written Opinion, International Application No. PCT/US2010/022592, dated Dec. 23, 2010, 6 pages.
Valjakka et al. (2002) "Crystal Structure of an in Vitro Affinity- and Specificity-Matured Anti-Testosterone Fab in Complex with Testosterone: Improved Affinity Results From Small Structural Changes Within the Variable Domains," J. Biological Chem. 277(46):44021-44027.
McCarthy et al. (2001) "Recombinant Technology: Altering the Fine Specificity of an Anti-Legionella Single Chain Antibody by a Single Amino Acid Insertion," J. Immunol. Meth., 251:137-149.
Webster (1888) "Engineering Antibody Affinity and Specificity," Inter. J. Canc. Supp.3:13-16.
Dabbs, (2002) "Diagnostic Immunohistochemistry," Churchill Livingstone, Philadelphia, PA pp. 17-19.
Amann et al. (1988) "Tightly Regulated tac Promoter Vectors Useful for the Expression of Unfused and Fused Proteins in *Escherichia coli*," Gene, 69:301-315.
Armour et al. (2003) "Differential Binding to Human FcγRIIa and FcγRIIb Receptors by Human IgG Wildtype and Mutant Antibodies," Mol. Immunol., 40:585-593.
Baldari et al. (1987) "A Novel Leader Peptide Which Allows Efficient Secretion of a Fragment of Human Interleukin 1β in *Saccharomyces cerevisiae*," EMBO J., 6(1):229-234.
Banerji et al. (1983) "A Lymphocyte-Specific Cellular Enhancer is Located Downstream of the Joining Region in Immunoglobulin Heavy Chain Genes," Cell, 33:729-740.
Beidler et al (1988) "Cloning and High Level Expression of a Chimeric Antibody with Specificity for Human Carcinoembryonic Antigen," J. Immunol., 141(11):4053-4060.
Better et al. (1988) "*Escherichia coli* Secretion of an Active Chimeric Antibody Fragment," Science, 240:1041-1043.

(Continued)

Primary Examiner — Hong Sang
(74) Attorney, Agent, or Firm — John M. Garvey; Pei Wu; K&L Gates LLP

(57) ABSTRACT

The present invention provides novel, rationally designed lowered affinity antibodies for use in various in vivo and in vitro applications. The antibodies of the present invention have variable domains that have been designed to reduce or eliminate the antigen binding activity of the parental antibody without altering the overall 3 dimensional antibody structure. Using the antibodies of the present invention in various assays allows researchers to distinguish effects that result from specific antigen-antibody interactions from other, non-specific antibody effects.

4 Claims, 9 Drawing Sheets

(56) References Cited

OTHER PUBLICATIONS

Bird et al. (1988) "Single-Chain Antigen-Binding Proteins," Science, 242:423-426.
Byrne et al. (1989) "Multiplex Gene Regulation: A Two-Tiered Approach to Transgene Regulation in Transgenic Mice," Proc. Natl. Acad. Sci. USA, 86:5473-5477.
Camper et al. (1989) "Postnatal Repression of the α-Fetoprotein Gene is Enhancer Independent," Genes & Develop., 3:537-546.
Capel et al. (1994) "Heterogeneity of Human IgG Fc Receptors," Immunomethods 4:25-34.
Chaiken (1981) "Semisynthetic Peptides and Proteins," in Critical Reviews in Biochemistry and Molecular Biology, 11:255-301.
Chothia et al. (1987) "Canonical Structures for the Hypervariable Regions of Immunoglobulins," J. Mol. Biol., 196:901-917.
Daëron (1997) "Fc Receptor Biology," Annu. Rev. Immunol., 15:203-234.
Edlund et al. (1985) "Cell-Specific Expression of the Rat Insulin Gene: Evidence for Role of Two Distint 5' Flanking Elements," Science, 230:912-916.
Goeddel (1990) "Systems for Heterologous Gene Expression," Methods in Enzymol., 185:3-7.
Gottesman (1990) "Minimizing Proteolysis in *Escherichia coli*: Genetic Solutions," Methods in Enzymol. 185:119-128.
Gutte et al. (1969) "The Total Synthesis of an Enzyme With Ribonuclease A Activity," in Communications to the Editor, J. Am. Chem. Soc. 91(2):501-502.
Huston et al. (1988) "Protein Engineering of Antibody Binding Sites: Recovery of Specific Activity in an Anti-digoxin Single-Chain Fv analogue Produced in *Escherichia coli*," Proc. Natl. Acad. Sci. USA, 85:5879-5883.
Jones et al. (1986) "Replacing the Complementarity-Determining Regions in a Human Antibody With Those From a Mouse," Nature 321:552-525.
Kaiser et al. (1989), "Peptide and Protein Synthesis by Segment Synthesis-Condensation," Science 243:187-192.
Kanda et al., (2006) "Comparison of Biological Activity Among Nonfucosylated Therapeutic IgG1 Antibodies With Three Different N-Linked Fc Oligosaccharides: the High-Mannose, Hybrid, and Complex Types," Glycobiology, 17 (1):104-118.
Kaufman et al. (1987) "Translational Efficiency of Polycistronic mRNAs and their Utilization to Express Heterologous Genes in Mammalian Cells," EMBO J., 6(1):187-193.
Kent (1988) "Chemical Sy8nthesis of Peptides and Proteins," Annu. Rev. Biochem. 57:957-989.
Kessel et al. (1990) "Murine Development Control Genes," Science 249:374-379.
Kjer-Nielsen et al. (2004) "Crystal Structure of the Human T Cell Receptor CD3εγ Heterodimer Complexed to the Therapeutic mAb OKT3," Proc Natl Acad Sci USA 101(20):7675-7680.
Kurjan et al. (1982) "Structure of a Yeast Pheromone Gene (MGα): A Putative α-Factor Precursor Contains Four Tandem Copies of Mature α-Factor," Cell 30:933-943.
Liu et al. (1987) "Chimeric Mouse-Human IgG1 Antibody That Can Mediate Lysis of Cancer Cells," Proc. Natl. Acad. Sci. USA, 84:3439-3443.
Liu et al. (1987) "Production of a Mouse-Human Chimeric Monoclonal Antibody to CD20 With Potent Fc-Dependent Biologic Activity," J. Immunol., 139(10):3521-3526.
Luckow et al. (1989) "High Level Expression of Nonfused Foreign Genes With *Autographa californica* Nuclear Polyhedrosis Virus Expression Vectors," Virology, 170:31-39.
MacCullum et al. (1996) "Antibody-Antigen Interactions: Contact Analysis and Binding Site Topography," J. Mol. Biol., 262:732-745.
Merrifield (1986) "Solid Phase Synthesis," Science, 232:341-347.
Midtvedt et al. (2003) "Individualized T Cell Monitored Administration of ATG Versus OKT3 in Steroid-Resistant Kidney Graft Rejection" Clin. Transplant.,17: 69-74.
Morrison (1985) "Transfectomas Provide Novel Chimeric Antibodies," Science 229:1202-1207.
Nishimura et al. (1987) "Recombinant Human-Mouse Chimeric Monoclonal Antibody specific for Common Acute Lymphocytic Leukemia Antigen," Cancer Res. 47:999-1005.
Pinkert et al. (1987) "An Albumin Enhancer Located 10 kb Upstream Functions Along With its Promoter to Direct efficient, Liver-Specific Expression in Transgenic Mice," Genes & Dev. 1:268-277-276.
Queen et al. (1983) "Immunoglobulin Gene Transcription is Activated by Downstraem Sequence Elements," Cell 33:741-748.
Queen et al. (1989) "A Humanized Antibody That Binds to the Interleukin 2 Receptor," Proc. Natl. Acad. USA, 86:10029-10033.
Raju (2008) "Terminal Sugars of Fc Glycans Influence Antibody Effector Functions of IgGs," Current Opinion in Immunol., 20:471-478.
Ravetch et al. (1991) "Fc Receptors," Annu. Rev. Immunol., 9:457-492.
Riechmann et al. (1998) "Reshaping Human Antibodies for Therapy," Nature 332:323-327.
Roopenian et al. (2007) "FcRn: The Neonatal Fc Receptor Comes of Age," Nat. Rev. Immunol. 7:715-725.
Schultz et al. (1987) "Expression and Secretion in Yeast of a 400-kDa Envelope Glycoprotein Derived From Epstein-Bar Virus," Gene 54:113-123.
Shaw et al. (1988) "Mouse/Human Chimeric Antibodies to a Tumor-Associated Antigen : Biologic Activity of the four Human IgG Subclasses," J. Natl. Cancer Inst. 80(19):1553-1559.
Smith et al. (1983) "Production of Human Beta Interferon in Insect Cells Infected With a Baculovirus Expression Vector," Mol. & Cell. Biol., 3(12):2156-2165.
Smith et al. (1988) "Single-Step Purification of Polypeptides Expressed in *Escherichia coli* as Fusions With Glutathione S-Transferase," Gene 67:31-40.
Studier et al. (1990) "[6] Use of T7 RNA Polymerase to Direct Expression of Cloned Genes," Methods in Enzymol., 185:60-89.
Sun et al. (1987) "Chimeric Antibody With Human Constant Regions and Mouse Variable Regions Directed Against Carcinoma-Associated Antigen," Proc. Natl. Acad. Sci. USA, 84:214-218.
Talbot et al. (1987) "Catabolism of Homologous Murine Monoclonal Hybridoma IgG Antibodies in Mice," Immuno., 60:485-489.
Thorpe et al. (1982) "The Preparation and Cytotoxic Properties of Antibody-Toxin Conjugates," Immunol. Rev., 62:119-158.
International Search Report and Written Opinion, International Application No. PCT/US2011/022998, dated Oct. 27, 2011, 9 pages.
Winkler et al. (2000) "Changing the Antigen Binding Specificity by Single Point Mutations of an Anti-p24 (HIV-1) Antibody," J. Immunol. 165:4505-4514.

* cited by examiner

ANTIBODY PRODUCTION OF OKT3 AND VARIANTS IN 293 T TRANSFECTION (ug/ml)

| LIGHT CHAIN | HEAVY CHAIN | WILD TYPE | CDRH1m | CDRH2m1 | CDRH2m2 | CDRH3m1 | CDRH3m2 |
|---|---|---|---|---|---|---|---|
| | | NA | T33A | Y50A/N52A/R55A/Y57A | R55A | Y99A/D101A/Y104A | D101A |
| WILD TYPE | NA | 5.8 | 6.7 | 2.8 | 3.4 | 2.5 | 1.4 |
| CDRL1m | S30A/Y31A | 4.7 | 7.7 | 2.9 | 4.1 | 3.0 | 2.9 |
| CDRL2m | D49A | 2.8 | 2.3 | 2.1 | 1.2 | 1.3 | 1.0 |
| CDRL3m | W90A/S91A | 4.3 | 2.9 | 3.5 | 2.5 | 3.3 | 1.9 |

SEQUENCE LISTING

```
<160> NUMBER OF SEQ ID NOS: 49

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Thr Phe Thr Arg Tyr Thr Met His
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Tyr Thr Phe Thr Arg Tyr Ala Met His
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Ile Asn Pro Ser Arg Gly Tyr Thr Asn Tyr Asn Gln Lys Phe Lys
1               5                   10                  15

Asp

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Ile Ala Pro Ser Ala Gly Ala Thr Asn Tyr Asn Gln Lys Phe Lys
1               5                   10                  15

Asp

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Ile Asn Pro Ser Ala Gly Tyr Thr Asn Tyr Asn Gln Lys Phe Lys
1               5                   10                  15

Asp
```

```
<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Tyr Asp Asp His Tyr Cys Leu Asp Tyr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Tyr Ala Asp His Ala Cys Leu Asp Tyr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Tyr Ala Asp His Tyr Cys Leu Asp Tyr
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Ala Ser Ser Ser Val Ser Tyr
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Ala Ser Ser Ser Val Ala Ala
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

```
Ile Tyr Asp Thr Ser Lys Leu
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ile Tyr Ala Thr Ser Lys Leu
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Gln Trp Ser Ser Asn Pro Phe Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Gln Ala Ala Ser Asn Pro Phe Thr
1               5

<210> SEQ ID NO 15
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Val Gln Leu Gln Gln Ser Gly Ala Glu Leu Ala Arg Pro Gly Ala
1               5                   10                  15

Ser Val Lys Met Ser Cys Lys Ala Ser
            20                  25

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Val Lys Gln Arg Pro Gly Gln Gly Leu Glu Trp Ile Gly
1               5                   10

<210> SEQ ID NO 17
<211> LENGTH: 32
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Lys Ala Thr Leu Thr Thr Asp Lys Ser Ser Thr Ala Tyr Met Gln
1               5                   10                  15

Leu Ser Ser Leu Thr Ser Glu Asp Ser Ala Val Tyr Tyr Cys Ala Arg
            20                  25                  30

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Trp Gly Gln Gly Thr Thr Leu Thr Val Ser Ser
1               5                   10

<210> SEQ ID NO 19
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ile Val Leu Thr Gln Ser Pro Ala Ile Met Ser Ala Ser Pro Gly
1               5                   10                  15

Glu Lys Val Thr Met Thr Cys
            20

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Asn Trp Tyr Gln Gln Lys Ser Gly Thr Ser Pro Lys Arg Trp
1               5                   10                  15

<210> SEQ ID NO 21
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Ser Gly Val Pro Ala His Phe Arg Gly Ser Gly Ser Gly Thr Ser
1               5                   10                  15

Tyr Ser Leu Thr Ile Ser Gly Met Glu Ala Glu Asp Ala Ala Thr Tyr
            20                  25                  30

Tyr Cys

<210> SEQ ID NO 22
```

-continued

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Phe Gly Ser Gly Thr Lys Leu Glu Ile Asn
1               5                   10

<210> SEQ ID NO 23
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 24
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105
```

```
<210> SEQ ID NO 25
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Ala Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 26
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Ala Ile Ala Pro Ser Ala Gly Ala Thr Asn Tyr Asn Gln Lys Phe
    50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 27
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27
```

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Ala Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 28
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ala Tyr Ala Asp His Ala Cys Leu Asp Tyr Trp Gly Gln Gly
            100                 105                 110

Thr Thr Leu Thr Val Ser Ser
        115

<210> SEQ ID NO 29
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe

```
                50                  55                  60
Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Ala Asp His Tyr Cys Leu Asp Tyr Trp Gly Gln Gly
                100                 105                 110

Thr Thr Leu Thr Val Ser Ser
        115

<210> SEQ ID NO 30
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Leu Gln Gln Ser Gly Ala Glu Leu Ala Arg Pro Gly Ala
 1               5                  10                  15

Ser Val Lys Met Ser Cys Lys Ala Ser Gly Tyr Thr Phe Thr Arg Tyr
                20                  25                  30

Ala Met His Trp Val Lys Gln Arg Pro Gly Gln Gly Leu Glu Trp Ile
                35                  40                  45

Gly Ala Ile Ala Pro Ser Ala Gly Ala Thr Asn Tyr Asn Gln Lys Phe
         50                  55                  60

Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
                100                 105                 110

Thr Thr Leu Thr Val Ser Ser
        115

<210> SEQ ID NO 31
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Gln Gln Ser Gly Ala Glu Leu Ala Arg Pro Gly Ala
 1               5                  10                  15

Ser Val Lys Met Ser Cys Lys Ala Ser Gly Tyr Thr Phe Thr Arg Tyr
                20                  25                  30

Ala Met His Trp Val Lys Gln Arg Pro Gly Gln Gly Leu Glu Trp Ile
                35                  40                  45

Gly Tyr Ile Asn Pro Ser Ala Gly Tyr Thr Asn Tyr Asn Gln Lys Phe
         50                  55                  60

Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
                100                 105                 110
```

Thr Thr Leu Thr Val Ser Ser
        115

<210> SEQ ID NO 32
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Ala Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 33
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Ala Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 34
<211> LENGTH: 119
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 34

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ala Tyr Ala Asp His Ala Cys Leu Asp Tyr Trp Gly Gln Gly
            100                 105                 110

Thr Thr Leu Thr Val Ser Ser
        115

<210> SEQ ID NO 35
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 36
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

```
Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
            115
```

<210> SEQ ID NO 37
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Gln Val Gln Leu Gln Gln Ser Gly Ala Glu Leu Ala Arg Pro Gly Ala
 1               5                  10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Tyr Tyr Ala Asp His Tyr Cys Leu Asp Tyr Trp Gly Gln Gly
            100                 105                 110

Thr Thr Leu Thr Val Ser Ser
            115
```

<210> SEQ ID NO 38
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Gln Val Gln Leu Gln Gln Ser Gly Ala Glu Leu Ala Arg Pro Gly Ala
 1               5                  10                  15

Ser Val Lys Met Ser Cys Lys Ala Ser Gly Tyr Thr Phe Thr Arg Tyr
                20                  25                  30

Ala Met His Trp Val Lys Gln Arg Pro Gly Gln Gly Leu Glu Trp Ile
            35                  40                  45

Gly Ala Ile Ala Pro Ser Ala Gly Ala Thr Asn Tyr Asn Gln Lys Phe
        50                  55                  60

Lys Asp Lys Ala Thr Leu Thr Thr Asp Lys Ser Ser Ser Thr Ala Tyr
 65                  70                  75                  80
```

```
Met Gln Leu Ser Ser Leu Thr Ser Glu Asp Ser Ala Val Tyr Tyr Cys
            85                  90                  95

Ala Arg Ala Tyr Ala Asp His Ala Cys Leu Asp Tyr Trp Gly Gln Gly
            100                 105                 110

Thr Thr Leu Thr Val Ser Ser
        115

<210> SEQ ID NO 39
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Ala Met His Trp Val Lys Gln Arg Pro Gly Gln Gly Leu Glu Trp Ile
            35                  40                  45

Gly Tyr Ile Asn Pro Ser Ala Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Ala Tyr Ala Asp His Ala Cys Leu Asp Tyr Trp Gly Gln Gly
            100                 105                 110

Thr Thr Leu Thr Val Ser Ser
        115

<210> SEQ ID NO 40
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Ala Met His Trp Val Lys Gln Arg Pro Gly Gln Gly Leu Glu Trp Ile
            35                  40                  45

Gly Ala Ile Ala Pro Ser Ala Gly Ala Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Tyr Tyr Ala Asp His Tyr Cys Leu Asp Tyr Trp Gly Gln Gly
            100                 105                 110

Thr Thr Leu Thr Val Ser Ser
        115
```

<210> SEQ ID NO 41
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Ala Met His Trp Val Lys Gln Arg Pro Gly Gln Gly Leu Glu Trp Ile
            35                  40                  45

Gly Tyr Ile Asn Pro Ser Ala Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Ala Asp His Tyr Cys Leu Asp Tyr Trp Gly Gln Gly
            100                 105                 110

Thr Thr Leu Thr Val Ser Ser
        115

<210> SEQ ID NO 42
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ala Ala Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105

<210> SEQ ID NO 43
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Ala Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105

<210> SEQ ID NO 44
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Ala Ala Ser Asn Pro Phe Thr
                85                  90                  95

Phe Gly Ser Gly Thr Lys Leu Glu Ile Asn
            100                 105

<210> SEQ ID NO 45
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ala Ala Met
            20                  25                  30

Asn Trp Tyr Gln Gln Lys Ser Gly Thr Ser Pro Lys Arg Trp Ile Tyr
        35                  40                  45

Ala Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn

<210> SEQ ID NO 46
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

```
Gln Ile Val Leu Thr Gln Ser Pro Ala Ile Met Ser Ala Ser Pro Gly
1               5                   10                  15
Glu Lys Val Thr Met Thr Cys Ser Ala Ser Ser Val Ala Ala Met
            20                  25                  30
Asn Trp Tyr Gln Gln Lys Ser Gly Thr Ser Pro Lys Arg Trp Ile Tyr
        35                  40                  45
Asp Thr Ser Lys Leu Ala Ser Gly Val Pro Ala His Phe Arg Gly Ser
    50                  55                  60
Gly Ser Gly Thr Ser Tyr Ser Leu Thr Ile Ser Gly Met Glu Ala Glu
65                  70                  75                  80
Asp Ala Ala Thr Tyr Tyr Cys Gln Gln Ala Ala Ser Asn Pro Phe Thr
                85                  90                  95
Phe Gly Ser Gly Thr Lys Leu Glu Ile Asn
                100                 105
```

<210> SEQ ID NO 47
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

```
Gln Ile Val Leu Thr Gln Ser Pro Ala Ile Met Ser Ala Ser Pro Gly
1               5                   10                  15
Glu Lys Val Thr Met Thr Cys Ser Ala Ser Ser Val Ser Tyr Met
            20                  25                  30
Asn Trp Tyr Gln Gln Lys Ser Gly Thr Ser Pro Lys Arg Trp Ile Tyr
        35                  40                  45
Ala Thr Ser Lys Leu Ala Ser Gly Val Pro Ala His Phe Arg Gly Ser
    50                  55                  60
Gly Ser Gly Thr Ser Tyr Ser Leu Thr Ile Ser Gly Met Glu Ala Glu
65                  70                  75                  80
Asp Ala Ala Thr Tyr Tyr Cys Gln Gln Ala Ala Ser Asn Pro Phe Thr
                85                  90                  95
Phe Gly Ser Gly Thr Lys Leu Glu Ile Asn
                100                 105
```

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

```
Gln Ile Val Leu Thr Gln Ser Pro Ala Ile Met Ser Ala Ser Pro Gly
1               5                   10                  15
```

```
Glu Lys Val Thr Met Thr Cys Ser Ala Ser Ser Ser Val Ala Ala Met
                20              25                  30

Asn Trp Tyr Gln Gln Lys Ser Gly Thr Ser Pro Lys Arg Trp Ile Tyr
        35                  40                  45

Ala Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65              70                  75                      80

Asp Ala Ala Thr Tyr Tyr Cys Gln Gln Ala Ala Ser Asn Pro Phe Thr
                85                  90                  95

Thr Phe Gly Ser Gly Thr Lys Leu Glu Ile Asn
                100             105

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(18)
<223> OTHER INFORMATION: This sequence may encompass 12-18 nucleotides

<400> SEQUENCE: 49
tttttttttt tttttttt                                            18
```

LOWERED AFFINITY ANTIBODIES AND USES THEREFOR

This application claims the benefit of PCT/US2010/022592, entitled "Novel Lowered Affinity Antibodies and Uses Therefor," filed on Jan. 29, 2010, and U.S. Provisional Application 61/148,578, filed Jan. 30, 2009, the entire contents of which are incorporated by reference

BACKGROUND OF THE INVENTION

Because of their ability to bind an antigen with a high degree of specificity, monoclonal antibodies are widely used as research, diagnostic, and therapeutic reagents. In addition to their specific binding to an antigen, monoclonal antibodies may activate the complement system and effector cells through their Fc region. In order to properly interpret an antibody's biological properties, proper controls are essential. Without proper controls, it is difficult to establish a causal relationship between an antibody's specific binding activity and the biochemical and biological effects of the antibody.

Control monoclonal antibodies currently in use include: 1. antibodies secreted by naturally occurring plasmacytoma, with no known target antigens; 2. antibodies raised against antigens from evolutionarily distant species, such as KLH (keyhole limpet hemocyanin); 3. antibodies reactive with a known target antigen that is distinct from the antigen of interest.

In each of these cases, the control antibodies used have a poorly defined variable domain and uncertain antigen specificities. And in the third case, there remains the issue of cross reactivity. Because of this, it is not uncommon to encounter problems such as cross reactivity or non-specific binding when currently available control antibodies are used. Furthermore, due to the lack of an ideal control antibody, research is often performed using formulation vehicles, such as normal saline, as a control. In such cases, it is difficult, if not impossible, to distinguish whether an observed biochemical and/or biological effect is a direct result of the specific antigen/antibody interaction, or a result of nonspecific effects, such as interactions and biological effects of other parts of the antibody molecule or contaminants present in the antibody preparation, such as the host cell proteins. For at least these reasons, there is currently a great need for improved, rationally designed control antibodies.

SUMMARY OF THE INVENTION

In one aspect, the present invention provides lowered affinity antibodies or antibody fragments, which are comprised of well-defined variable domains that lack antigen affinity but maintain a native antibody structure. The novel lowered affinity antibodies or antibody fragments when used as controls allow researchers to distinguish effects that result from specific antigen-antibody interactions as opposed to non-specific antibody effects. Antibodies or antibody fragments of the present invention are therefore useful as controls in a wide range of applications that utilize antibody reagents, including flow cytometry, immunoblotting (e.g., dot blotting, western blotting), immunohistochemistry, immunoprecipitation, ELISA, fluorescence microscopy, cellular isolation, cellular purification, protein purification, and other antibody based assays. Antibodies or antibody fragments of the invention are also useful as controls in in vitro and in vivo assays in which antibodies are used to elicit a specific cellular response (e.g., cellular proliferation, cellular differentiation, apoptosis, etc.) and for therapeutic applications, both in humans and in non-human animals.

In some embodiments, the antibodies or antibody fragments of the invention are comprised of a heavy chain variable region that contains a framework 1 region (FRH1); a first complementary determining region (CDRH1), which is exemplified by SEQ ID NO: 1 or SEQ ID NO: 2; a framework 2 region (FRH2); a second complementary determining region (CDRH2), which is exemplified by SEQ ID NO: 3, SEQ ID NO: 4 or SEQ ID NO: 5; a framework 3 region (FRH3); a third complementary determining region (CDRH3), which is exemplified by SEQ ID NO: 6, SEQ ID NO: 7 or SEQ ID NO: 8 and a framework 4 region (FRH4); wherein the antibody has no specific binding affinity to the human TCR/CD3 complex. In some embodiments FRH1, FRH2, FRH3 or FRH4 is selected from the group consisting of SEQ ID NOs: 15, 16, 17 and 18. In certain other embodiments the heavy chain variable region has an amino acid sequence as set forth in any of SEQ ID NOs: 25-41, In some embodiments, the antibodies or antibody fragments of the invention comprises a light chain variable region containing a framework 1 region (FRL1), a first complementary determining region (CDRL1), which is exemplified by SEQ ID NO: 9 or SEQ ID NO: 10, a framework 2 region (FRL2), a second complementary determining region (CDRL2), which is exemplified by SEQ ID NO: 11 or SEQ ID NO: 12, a framework 3 region (FRL3), a third complementary determining region (CDRL3), which is exemplified by SEQ ID NO: 13 and SEQ ID NO: 14 and a framework 4 region (FRL4). In some embodiments FRL1, FRL2, FRL3 or FRL4 is selected from the group consisting of SEQ ID NOs: 19, 20, 21 and 22. In certain other embodiments the light chain variable region has an amino acid sequence as set forth in SEQ ID NOs: 42-48.

In some embodiments, the antibodies of the invention further comprise a heavy chain constant domain selected from the group consisting of IgM, IgG, IgA, IgD and IgE and/or a light chain constant domain selected from the group consisting of kappa and lambda light chains. In some embodiments the heavy chain is aglycosylated or displays various non-human glycoforms. In certain embodiments the antibody is humanized. In a preferred embodiment, the antibody is human. In certain other embodiments, the antibody is conjugated to a detectable moiety.

In some embodiments, the antibodies or antibody fragments of the invention have a reduced or non-detectable specific binding affinity to a target antigen as compared to a reference antibody. In some other embodiments, the antibodies or antibody fragments have a 50 fold or greater reduction of specific binding affinity to a target antigen. In some other embodiments, the antibodies or antibody fragments have a 100 fold or greater reduction of specific binding affinity to a target antigen. In yet some other embodiments, the antibodies or antibody fragments have a 500 fold or greater reduction of specific binding affinity to a target antigen.

In some embodiments, the antibody or antibody fragment is selected from the group consisting of: (a) a whole immunoglobulin molecule; (b) an scFv; (c) an Fab fragment; (d) an Fab' fragment; (e) an F(ab')2; (f) an Fv; (g) an Fd fragment; and (h) a disulfide linked Fv.

In another aspect, the present invention provides a purified mammalian cell having OKT3 expression plasmids which express heavy and light chains of the antibody or antibody fragment sequences of SEQ ID NOs 1-22. In some embodiments, the cells are human 293 cells.

BRIEF DESCRIPTION OF THE DRAWINGS

FIG. 3 shows antibody production of OKT3 and some exemplary lowered affinity antibodies of the invention.

DETAILED DESCRIPTION OF THE INVENTION

Figure 1:
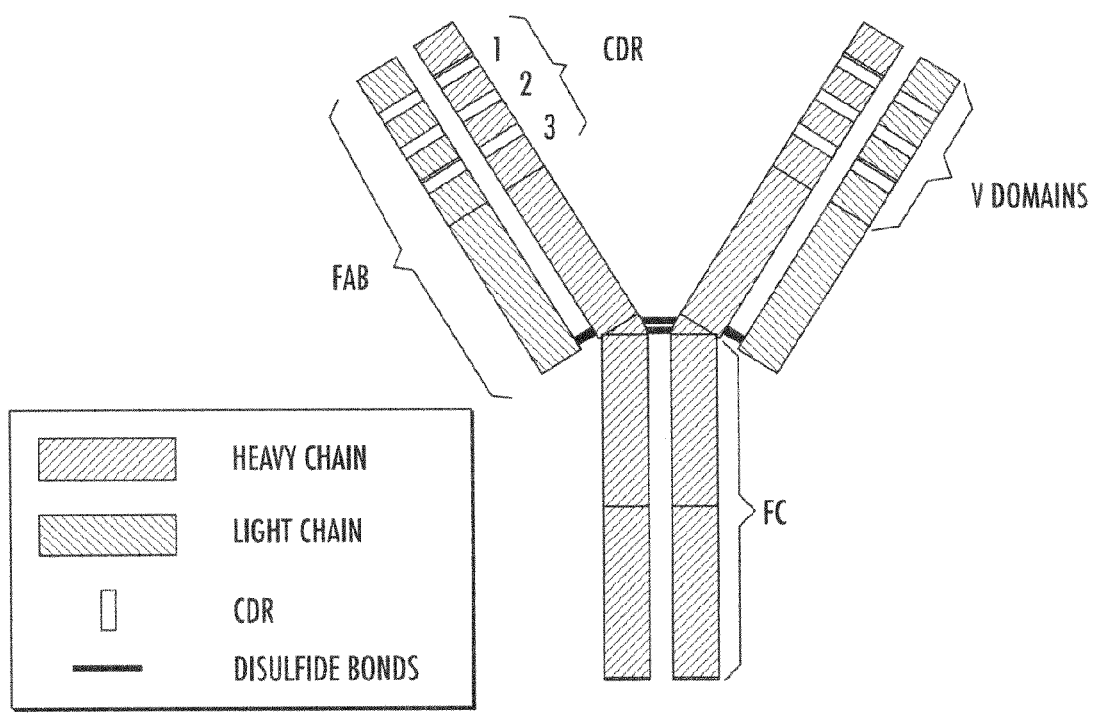
FIG. 1 shows an exemplary schematic diagram of an antibody structure, including the CDR regions, variable domains, the Fab domain and the Fc domain.
Figure 2:
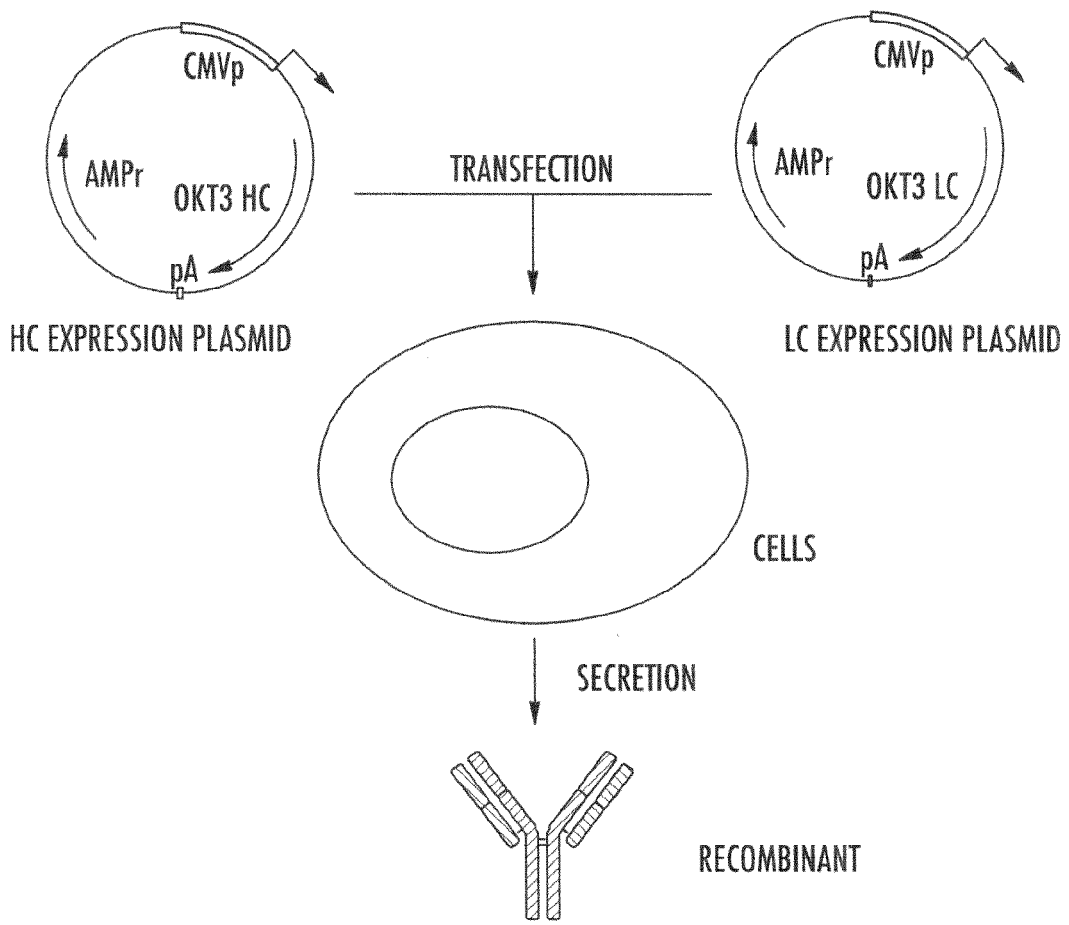
FIG. 2 shows a schematic representation of an exemplary method of recombinant antibody production.

The present invention provides novel, lowered affinity antibodies, having well characterized variable domains that reduce or eliminate antigen binding without substantially altering the three dimensional structure of the antibody. In order for the present invention to be more readily understood, certain terms and phrases are defined below as well as throughout the specification.

The term "antibody" is well understood in biological and biomedical field and commonly refers to whole antibodies and any antibody fragment, or single chain thereof. Antibodies are glycoproteins secreted by specialized B lymphocytes known as plasma cells. They are also referred to as immunogobulins (Ig) because they contain a common structural domain found in many proteins. Antibodies most likely comprise two heavy (H) chains and two light (L) chains typically connected by disulfide bonds, or an antigen binding portion thereof. Each heavy chain is comprised of a heavy chain variable region ($V_H$) and a heavy chain constant region. Each light chain is also comprised of a variable region ($V_L$) and a constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

The present invention includes antibody fragments as well. Examples of antibody fragments include (i) a Fab fragment, a monovalent fragment consisting of the $V_H$, $V_L$, CL and CH1 domains; (ii) a F(ab')$_2$ fragment, a bivalent fragment comprising two Fab fragments linked by disulfide bridges at the hinge region; (iii) a Fd fragment consisting of the $V_H$ and CH1 domains; (iv) a Fv fragment consisting of the $V_H$ and $V_L$ domains of a single arm of an antibody, (v) a dAb fragment (Ward et al., (1989) Nature 341:544 546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); see e.g., Bird et al. (1988) Science 242:423 426; and Huston et al. (1988) Proc. Natl. Acad. Sci. USA 85:5879 5883). Such single chain antibodies are also intended to be encompassed within the term "antigen-binding portion" of an antibody. As used herein, "antibody" and "antibody fragments" are used interchangeably to describe the invention unless specifically stated otherwise.

The term "hypervariable region," "HVR," or "HV," refers to the regions of an antibody-variable domain that are hypervariable in sequence and form structurally defined loops. Generally, antibodies comprise six HVRs; three in the VH (H1, H2, H3), and three in the VL (L1, L2, L3). In an antibody molecule, the three HVRs of a VH domain and the three HVRs of a VL domain are brought together in three-dimensional structure to form an antigen binding surface. Because these sequences form a surface that is complementary to the three dimensional structure of the target antigen, the HVRs are also known as complementarity-determining regions (CDRs).

The terms "CDR", and its plural "CDRs", refer to a complementarity determining region (CDR) of which three make up the binding character of a light chain variable region (CDRL1, CDRL2 and CDRL3) and three make up the binding character of a heavy chain variable region (CDRH1, CDRH2 and CDRH3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat, Chothia, and/or MacCallum et al., (Kabat et al., in "Sequences of Proteins of Immunological Interest," 5$^{th}$ Edition, U.S. Department of Health and Human Services, 1992; Chothia et al., J. Mol. Biol., 1987, 196: 901; and Mac-Callum et al., J. Mol. Biol., 1996, 262: 732, each of which is incorporated by reference in its entirety).

"Framework region" or "FR" residues are those variable-domain residues other than the HVR residues as herein defined. Exemplary framework regions are provided as SEQ ID NOs. 15-22.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include IgG, IgM, IgA, IgD and IgE.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the Fc gamma RI, Fc gamma RII, and Fc gamma RIII subclasses, including allelic variants and alternatively spliced forms of these receptors, Fc gamma RII receptors include Fc gamma RHA (an "activating receptor") and Fc gamma RIIA (an "inhibiting receptor"), which have similar amino acid sequences that differ primarily in the cytoplasmic domains thereof. Activating receptor Fc gamma RIIA contains an immunoreceptor tyrosine-based activation motif (ITAM) in its cytoplasmic domain. Inhibiting receptor Fc gamma RIIB contains an immunoreceptor tyrosine-based inhibition motif (ITIM) in its cytoplasmic domain. (see M. Daëron, Annu. Rev. Immunol. 15:203-234 (1997). FcRs are reviewed in Ravetch and Kinet, Annu. Rev. Immunol. 9: 457-92 (1991); Capel et al., Immunomethods 4: 25-34 (1994); and de Haas et al., J. Lab. Clin. Med. 126: 330-41 (1995). Other FcRs, including those binding to other isotypes as well as those to be identified in the future, are encompassed by the term "FcR" herein.

Antibodies may be xenogeneic, allogeneic, or syngeneic; or modified forms thereof (e.g., humanized, chimeric, etc.). Antibodies may also be fully human. The term "monoclonal antibody" as used herein, refers to an antibody which displays a single binding specificity and affinity for a particular epitope. Accordingly, the term "human monoclonal antibody" refers to an antibody which displays a single binding specificity and which has variable and constant regions derived from human germline or non-germline immunoglobulin sequences. In one embodiment, human monoclonal antibodies are produced by a hybridoma which includes a B cell obtained from a transgenic non-human animal, e.g., a transgenic mouse, having a genome comprising human heavy and light chain transgenes fused to an immortalized cell.

In some embodiments of the invention, antibodies, or fragments thereof, are modified to reduce or eliminate potential glycosylation sites. Such modified antibodies are often referred to as "aglycosylated" antibodies. In order to improve the binding affinity of an antibody or antigen-binding fragment thereof, glycosylation sites of the antibody can be altered, for example, by mutagenesis (e.g., site-directed mutagenesis). "Glycosylation sites" refer to amino acid residues which are recognized by a eukaryotic cell as locations for the attachment of sugar residues. The amino acids where carbohydrate, such as oligosaccharide, is attached are typically asparagine (N-linkage), serine (O-linkage), and threonine (O-linkage) residues. In order to identify potential glycosylation sites within an antibody or antigen-binding fragment, the sequence of the antibody is examined, for example, by using publicly available databases such as the website provided by the Center for Biological Sequence Analysis for predicting N-linked and O-linked glycosylation sites. Additional methods for altering glycosylation sites of antibodies are described in U.S. Pat. Nos. 6,350,861 and 5,714,350. Further, antibody glycosylation can be influenced by the cell in which it is produced, the conformation of an antibody and the cell culture conditions. The preferred cell expression system of the invention is human cell expression system.

The term "humanized antibody" refers to an antibody that consists of the CDR of antibodies derived from mammals other than human, and the FR region and the constant region of a human antibody. A humanized antibody is useful as an effective component in a therapeutic agent since antigenicity of the humanized antibody in human body is lowered. It is an objective of the present invention to design lowered affinity antibodies to humanized antibodies in the context of therapeutic applications.

The term "recombinant antibody" includes all antibodies that are prepared, expressed, created or isolated by recombinant means, such as (a) antibodies isolated from an animal (e.g., a mouse) that is transgenic or transchromosomal for immunoglobulin genes or a hybridoma prepared therefrom (described further in Section I, below), (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences. Such recombinant antibodies have variable and constant regions derived from germline and/or non-germline immunoglobulin sequences. In certain embodiments, however, such recombinant antibodies can be subjected to in vitro mutagenesis (or, when an animal transgenic for Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the germline repertoire in vivo.

The term "bispecific monoclonal antibody" refers to a monoclonal antibody having dual specificity in their binding arms to two different types of antigen. Bispecific monoclonal antibodies do not occur naturally; they have to be made with recombinant DNA or cell fusion technology. With this approach, it is possible for such an antibody to simultaneously bind to a cytotoxic cell (using a receptor like CD3) and a cancer target cell (like CD19), leading to more efficient killing of target cancer cells. It is the objective of the present invention to design lowered affinity antibodies to bispecific monoclonal antibodies such that one or both arms of the biospecific antibody will have reduced or eliminated affinity to an antigen.

The term "$K_D$" is intended to refer to the dissociation equilibrium constant of a particular antibody-antigen interaction. The measure of the binding strength of an antibody for a monovalent epitope is referred to as affinity. In some instances, antibodies can form multivalent interactions with antigen. In such cases, the apparent dissociation equilibrium constant of an antibody/antigen interaction may vary from the monovalent dissociation constant.

Affinity varies depending on the non-covalent bonds that exist between the antigen combining site on the antibody and the antigenic determinant or epitope of the specific antigen. In a typical situation, antibodies are used for their specific binding properties and the antibody binds with an affinity ($K_D$) of approximately less than $10^{-7}$ M, such as approximately less than $10^{-8}$ M, $10^{-9}$ M or $10^{-10}$ M or even lower when determined, for example, by surface plasmon resonance (SPR) technology in a BIACORE instrument using recombinant proteins as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen". An antibody that has "lowered affinity" refers to a $K_D$ of approximately greater than $10^{-7}$ M, such as approximately 10, or 100, or 1000 fold greater than $10^{-7}$ M. It is the objective of the present invention to design an antibody with little or no specific binding to an antigen. In some embodiments the antibodies of the invention have a dissociation constant ($K_D$) of greater than or equal to about $10^{-7}$. More preferably, the antibodies of the invention have a dissociation constant ($K_D$) of greater than or equal to about $10^{-6}$. Most preferably, the antibodies of the invention have no detectable specific binding towards a defined antigen.

Depending on the Ig class, up to five structural molecules may be combined to form any one antibody. In mammals, there are five classes of Ig (IgG, IgM, IgA, IgD, and IgE); and in avians, there are three classes (IgY, IgM, and IgE). In select mammals, IgG and IgA are further subdivided into subclasses, referred to as isotypes, due to polymorphisms in the conserved regions of the heavy chain.

The term "nucleic acid molecule" or "polynucleotide" is intended to include DNA molecules and RNA molecules. A nucleic acid molecule may be single-stranded or double-stranded, but preferably is double-stranded DNA.

The present invention also encompasses "conservative sequence modifications" of the sequences set forth in the figures, including nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced into the sequence set forth in the figures by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

Accordingly, antibodies encoded by the heavy and light chain variable region nucleotide sequences disclosed herein and/or containing the heavy and light chain variable region amino acid sequences disclosed herein include substantially similar antibodies encoded by or containing similar sequences which have been conservatively modified. Further discussion as to how such substantially similar antibodies can be generated based on the sequences (i.e., heavy and light chain variable regions) disclosed herein is provided below.

The nucleic acid compositions of the present invention may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

Various aspects of the invention are described in further detail in the following subsections.

I. Lowered Affinity Antibodies

Lowered affinity antibodies of the present invention are antibodies that were rationally designed to eliminate or reduce binding to an antigen. A currently preferred lowered affinity antibody is one that resembles the wild type (native) antibody in every respect except for the CDR region and shows little discernable 3 dimensional structural change relative to the wild type antibody. An exemplary antibody is one that demonstrates a decreased binding affinity to an antigen by 10 fold. Preferably, a lowered affinity antibody binds to an antigen with a decreased binding affinity to an antigen by 100 fold. More preferably, a lowered affinity antibody binds to an antigen with a decreased binding affinity to an antigen by 1000 fold. Most preferably, a lowered affinity antibody shows no substantial binding to an antigen, and no specific binding to an antigen is detectible over the background binding levels. The affinity can be measured by common experimental methods including surface Plasmon resonance, or radio ligand binding assay, or flow cytometry. Lowered affinity antibodies of the present invention are useful as control reagents for their wild type (native) counterpart that retains specific binding to an antigen in many in vivo and in vitro applications that involve the use of antibodies.

Lowered affinity antibodies of the invention can be produced using a variety of known techniques, such as the recombinant DNA techniques and other standard molecular and cell biology techniques.

Recombinant lowered affinity antibodies can be made using recombinant DNA techniques and gene transfection methods well known in the art (Morrison, S. (1985) Science 229: 1202). For example antibody-encoding polynucleotides can be amplified by standard molecular biology techniques (e.g. polymerase chain reaction) and ligated into an expression vector (e.g. pME). Expression vectors encoding the cloned antibody heavy and light chain genes can be transfected into host cells (e.g. 293T cells, CHO-cells) using techniques known in the art (e.g. calcium phosphate precipitation, electroporation, lipofection).

In another embodiment lowered affinity antibodies can be generated as chimeric antibodies in which the variable regions of the antibody heavy and/or light chains are fused to constant domains from various species. In addition, humanized lowered affinity antibodies can be made according to standard protocols such as those disclosed in U.S. Pat. No. 5,565,332. In another embodiment, antibody chains can be produced by recombination between vectors comprising nucleic acid molecules encoding a fusion of a polypeptide chain of a specific antibody chain and a component of a replicable generic display package and vectors containing nucleic acid molecules encoding a second polypeptide chain of a single binding pair member using techniques known in the art, e.g., as described in U.S. Pat. Nos. 5,565,332, 5,871, 907, or 5,733,743.

Lowered affinity antibodies of the invention can be produced using recombinant DNA techniques known in the art, for example using methods described in Robinson et al. International Patent Publication PCT/US86/02269; Akira et al. European Patent Application 184,187; Taniguchi, M. European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad.

Sci. 84:214-218; Nishimura et al. (1987) Cancer Res. 47:999-1005; Wood et al. (1985) Nature 314:446-449; and Shaw et al. (1988) J. Natl. Cancer Inst. 80:1553-1559); Morrison, S. L. (1985) Science 229:1202-1207; Oi et al. (1986) Biotechniques 4:214; Winter U.S. Pat. No. 5,225,539; Jones et al. (1986) Nature 321:552-525; Verhoeyan et al. (1988) Science 239:1534; and Beidler et al. (1988) J. Immunol. 141:4053-4060.

In still another aspect of the invention, partial or known antibody sequences can be used to generate and/or express new antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of a specific antibody by constructing expression vectors that include CDR sequences from the specific antibody grafted onto framework sequences from a different antibody with different properties (see, e.g., Riechmann, L. et al., 1998, Nature 332:323 327; Jones, P. et al., 1986, Nature 321:522 525; and Queen, C. et al., 1989, Proc. Natl. Acad. See. U.S.A. 86:10029 10033). Such framework sequences can be obtained from public DNA databases that include germline or non-germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999). Partial heavy and light chain sequence spanning the CDR regions is typically sufficient for this purpose. The partial sequence is used to determine which germline and/or non-germline variable and joining gene segments contributed to the recombined antibody variable genes. The germline and/or non-germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons. The process can also be used to screen libraries of particular immunoglobulin encoding sequences in one species (e.g., human) to design cognate immunoglobulin encoding sequences from known antibody sequence in another species (e.g., mouse).

The CDR 1, 2, and/or 3 regions of the engineered antibodies described above can comprise the exact amino acid sequence(s) as those of variable regions of the present invention disclosed herein. However, the ordinarily skilled artisan will appreciate that some deviation from the exact CDR sequences may be possible while still retaining its utility as a control antibody (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of the present invention.

The interaction of antibodies and antibody-antigen complexes with cells of the immune system triggers a variety of responses, collectively called effector functions, through a variety of mechanisms, including, for example, by binding to Fc receptors (FcRs) and/or to the C1q component of the complement system. Effector functions may trigger cytokine release, phagocytosis, endocytosis, cytotoxicity (both antibody-dependant cell-mediated cytotoxicity and complement-mediated cytotoxicity), down regulation of cell surface antigens, and/or apoptosis of targeted cells. In certain instances, antibody effector functions may result in undesirable consequences, including, for example, unwanted inflammation and/or elimination of antigen-bearing cells. Therefore, it may be desirable in many instances to modify antibodies in order to reduce or alter antibody effector functions. Accordingly, the present invention further relates to lowered affinity antibodies with altered effector functions.

Interactions of Fc and FcRs have been mapped to several peptide segments within the Fc region. For example, P238 and S239 of the 231-239 (EU numbering) segments have been identified to be involved in FcR binding. In addition, 316-338 and 274-301 segments separately were found to be critical for Fe binding to FcγRI and FcγRIII, respectively. It has been shown that effector functions can be modified by combining critical segments of the Fc region from different antibody subtypes (such as IgG2 and IgG4) in order to generate antibodies that produce the desired effector functions (Armour K L et al., Mol. Immunol. 40, 585-593, 2003). Accordingly, the present invention includes lowered affinity antibodies that contain modifications that result in altered effector functions. For example, antibodies with altered ability to induce complement mediated cytotoxicity can be generated through modification of the 213-238 segment at the N-terminal of the CH2 region and/or the 318-331 segment at the C-terminal of the CH2 region (i.e. K322A and P329A substitutions can be generated in IgG1 antibodies to reduce binding of the antibodies to C1a and thereby reducing complement mediated cytotoxicity). In another example, lowered affinity antibodies of the present invention can includes modifications of one or more of these critical amino acid residues for binding to one type of FcR while retaining the ability to bind one or more other types of FcR and/or C1q.

Glycosylation of the canonical Asn297 residue (N—X—S/T signature triplet peptide) at the CH$_2$ of the Fc region also contributes to antibody binding of FcRs and C1q. Removal of this N-glycan reduces antibody bindings to Fc receptors and the C1q complement. Hence, altering glycosylation at Asn297 at the CH2 region of the antibody is another approach to modulate the effector functions of an antibody (Raju, T S, Current Opinion in Immunol. 20, 471-478, 2008). In addition, the heterogeneity of Asn297-linked glycans can affect antibody binding to FcRs and C1q. Importantly, loss of the canonical glycans compromises antibody binding to FcRs, but does not affect antibody half life (reviewed in Roopenian D C and Akilesh S. Nat. Rev. Immunol. 9, 715-725, 2007). Effector function modification through removal of glycans can be used in combination with the mutated FcR and/or C1q binding sites described above.

In contrast to the reduced effector functions in antibodies with reduced levels of canonical glycans, antibodies with reduced levels of fucose in their sugar chains have enhanced binding to FcγRIIIa. As FcγRIIIa is an important Fc receptor for antibody dependant cell mediated cytotoxicity, low-fucose antibodies exhibit higher ADCC response compared to the conventionally high-fucose antibodies (Kanda S et al, Glycobiology, 17, 104-118, 2007).

Thus, the present invention includes lowered affinity antibodies carrying altered glycosylation. The alteration of N-glycans in the CH2 domain of the heavy chain Fc region may be accomplished by any technique known in the art, including, for example, by mutation of the canonical Asn residue at 297 position, mutation of the canonical Ser or Thr residue at 299 position (to eliminate the tri-peptide N-glycosylation motif, N—X—S/T), enzymatic removal of the glycans (use of PNGase F (peptide N-glycohydrolase)), metabolic blockade of in situ glycosylation (such as use of ER glycosylation inhibitor, tunicamycin, in culture of antibody producing cells), or production of afucosylated antibodies in host cell lines that are deficient in fucosyl transferase (Kanda S et al, Glycobiology, 17, 104-118, 2007). The glycosylation sites may be altered by culturing in yeast, bacteria, or other non-human eukaryotes.

II. Isolated Nucleic Acid Molecules

One aspect of the invention pertains to isolated nucleic acid molecules that encode polypeptides of the present invention as well as nucleic acid fragments sufficient for use as hybridization probes to identify nucleic acid molecules encoding these polypeptides and fragments for use as PCR primers for the amplification or mutation of the nucleic acid molecules. The term "nucleic acid molecule" or "polynucleotide" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule of the present invention can be isolated using standard molecular biology techniques and the sequence information provided herein. For example, a nucleic acid molecule of the invention can be isolated by the polymerase chain reaction (PCR) using synthetic oligonucleotide primers designed based upon the sequences of the invention.

A nucleic acid molecule of the invention can be amplified using cDNA, mRNA or, alternatively, genomic DNA as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to nucleic acid sequences of the invention can be prepared by standard synthetic techniques, e.g., using an automated DNA synthesizer.

An isolated nucleic acid molecule encoding a polypeptide identical to the polypeptides of the invention can be created by introducing one or more nucleotide substitutions, additions or deletions into the nucleotide sequences of the invention such that one or more amino acid substitutions, additions or deletions are introduced into the encoded polypeptide. Mutations can be introduced into nucleic acid molecules of the present invention by standard techniques, such as site-directed mutagenesis and PCR-mediated mutagenesis. In one embodiment, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), non-polar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a polypeptide of the invention (e.g., those in FIGS. 2-7) can be replaced with another amino acid residue from the same side chain family. Alternatively, in another embodiment, mutations can be introduced randomly along all or part of a nucleic acid molecule(s) of the present invention, such as by saturation mutagenesis, and the resultant mutants can be screened for biological activity to identify mutants that retain activity. Following mutagenesis of a nucleic acid molecule of the present invention, the encoded polypeptide can be expressed recombinantly and the activity of the polypeptide can be determined.

The expression characteristics of a nucleic acid molecules of the present invention within a cell line or microorganism may be modified by inserting a heterologous DNA regulatory element into the genome of a stable cell line or cloned microorganism such that the inserted regulatory element is operatively linked with the a nucleic acid molecules of the present invention. For example, a heterologous regulatory element may be inserted into a stable cell line or cloned microorganism, such that it is operatively linked with a nucleic acid molecules of the present invention, using techniques, such as targeted homologous recombination, which are well known to those of skill in the art, and described, e.g., in Chappel, U.S. Pat. No. 5,272,071; PCT publication No. WO 91/06667, published May 16, 1991.

III. Isolated Polypeptide Molecules

One aspect of the invention pertains to isolated polypeptides of the present invention (e.g., those that encode the lowered affinity antibodies of the present invention). In one embodiment, polypeptides of the present invention can be isolated from cells or tissue sources by an appropriate purification scheme using standard protein purification techniques. In another embodiment, polypeptides of the present invention are produced by recombinant DNA techniques. Alternatively, polypeptides of the present invention can be chemically synthesized using standard peptide synthesis techniques.

An "isolated" or "purified" polypeptide is substantially free of cellular material or other contaminating proteins from the cell or tissue source from which the polypeptides of the present invention is derived, or substantially free from chemical precursors or other chemicals when chemically synthesized. The language "substantially free of cellular material" includes preparations of polypeptide(s) of the present invention in which the polypeptide is separated from cellular components of the cells from which it is isolated or recombinantly produced. In one embodiment, the language "substantially free of cellular material" includes preparations of polypeptide(s) of the present invention having less than about 30% (by dry weight) of proteins not of the present invention (also referred to herein as a "contaminating protein"), more preferably less than about 20% of proteins not of the present invention, still more preferably less than about 10% of proteins not of the present invention, and most preferably less than about 5% of proteins not of the present invention. When polypeptides of the present invention are recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of polypeptide(s) of the present invention in which the polypeptide is separated from chemical precursors or other chemicals which are involved in the synthesis of the polypeptide. In one embodiment, the language "substantially free of chemical precursors or other chemicals" includes preparations of polypeptide(s) of the present invention having less than about 30% (by dry weight) of chemical precursors or of proteins not of the present invention, more preferably less than about 20% chemical precursors or of proteins not of the present invention, still more preferably less than about 10% chemical precursors or of proteins not of the present invention, and most preferably less than about 5% chemical precursors or of proteins not of the present invention.

In another embodiment, polypeptide(s) of the present invention (e.g., those that encode the lowered affinity antibodies of the present invention) has an amino acid sequence that includes one or more of SEQ ID NO: 1-14.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In one embodiment, the length of a reference sequence aligned for comparison purposes is at least 30%, preferably at least 40%, more preferably at least 50%, even more preferably at least 60%, and even more preferably at least 70%, 80%, 90%, 95%, 96%, 97%, 98%, 99%, 99.5%, or 99.9% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The amino acid sequences of the described polypeptide(s) will enable those of skill in the art to produce corresponding polypeptides. Such polypeptides can be produced in prokaryotic or eukaryotic host cells by expression of polynucleotides encoding a polypeptide(s) of the present invention. Alternatively, such polypeptides can be synthesized by chemical methods. Methods for expression of heterologous polypeptides in recombinant hosts, chemical synthesis of polypeptides, and in vitro translation are well known in the art and are described further in Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91:501; Chaiken I. M. (1981) CRC Crit. Rev. Biochem. 11:255; Kaiser et al. (1989) Science 243:187; Merrifield, B. (1986) Science 232:342; Kent, S. B. H. (1988) Annu. Rev. Biochem. 57:957; and Offord, R. E. (1980) Semisynthetic Proteins, Wiley Publishing, which are incorporated herein by reference).

IV. Recombinant Expression Vectors and Host Cells

Another aspect of the invention pertains to vectors, preferably expression vectors, containing a nucleic acid molecule encoding a polypeptide of the present invention (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) Methods Enzymol. 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors of the invention can be designed for expression of polypeptides of the present invention in prokaryotic or eukaryotic cells. For example, the polypeptides can be expressed in bacterial cells such as E. coli, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of polypeptides in prokaryotes is most often carried out in *E. coli* with vectors containing constitutive or inducible promoters directing the expression of either fusion or non-fusion proteins. Fusion vectors add a number of amino acids to a polypeptide encoded therein, usually to the amino terminus of the recombinant polypeptide. Such fusion vectors typically serve three purposes: 1) to increase expression of recombinant polypeptide; 2) to increase the solubility of the recombinant polypeptide; and 3) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant polypeptide.

Examples of suitable inducible non-fusion *E. coli* expression vectors include pTrc (Amann et al. (1988) Gene 69:301-315) and pET 1 id (Studier et al. (1990) Methods Enzymol. 185:60-89). Target gene expression from the pTrc vector relies on host RNA polymerase transcription from a hybrid trp-lac fusion promoter. Target gene expression from the pET 11 d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant polypeptide expression in *E. coli* is to express the polypeptide in host bacteria with impaired capacity to proteolytically cleave the recombinant polypeptide (Gottesman, S. (1990) Methods Enzymol. 185:119-128). Another strategy is to alter the nucleic acid sequence of the nucleic acid to be inserted into an expression vector so that the individual codons for each amino acid are those preferentially utilized in *E. coli* (Wada et al. (1992) Nucleic Acids Res. 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and picZ (Invitrogen Corp, San Diego, Calif.).

Alternatively, polypeptides of the present invention (e.g., FIGS. 2-7) can be expressed in insect cells using baculovirus expression vectors. Baculovirus vectors available for expression of polypeptides in cultured insect cells (e.g., Sf9 cells) include the pAc 'series (Smith et al. (1983) Mol. Cell. Biol. 3:2156-2165) and the pVL series (Lucklow and Summers (1989) Virology 170:31-39).

In yet another embodiment, a nucleic acid of the present invention (e.g., FIGS. 2-7) is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example by the murine hox promoters (Kessel and Gruss (1990) Science 249:374-379) and the .alpha.-fetoprotein promoter (Camper and Tilghman (1989) Genes Dev. 3:537-546).

Another aspect of the invention pertains to host cells into which a nucleic acid molecule of the present invention is introduced within a recombinant expression vector or a nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a polypeptide of the present invention can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as the polynucleotide of the invention or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a polypeptide of the present invention. Accordingly, the invention further provides methods for producing a polypeptide of the present invention using the host cells of the present invention. In one embodiment, the method comprises culturing the host cell of the invention (into which a recombinant expression vector encoding a polypeptide of the present invention has been introduced) in a suitable medium such that a polypeptide of the present invention is produced. In another embodiment, the method further comprises isolating a polypeptide of the present invention from the medium or the host cell.

The host cells of the invention can also be used to produce non-human transgenic animals, as described below.

V. Antibody Conjugates/Immunotoxins

In another aspect, the present invention features lowered affinity antibodies conjugated to a therapeutic moiety, such as a cytotoxin, a drug (e.g., an immunosuppressant) or a radioisotope, which can be used as controls in pre-clinical and/or clinical studies designed to examine the safety and efficacy of specific antibodies conjugated similarly for various therapeutic applications. Specific antibodies conjugated to a cytotoxin are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Specific antibodies can also be conjugated to a radioisotope, e.g., radioactive iodine, to generate cytotoxic radiopharmaceuticals for treating a related disorder, such as a cancer.

Conjugated lowered affinity antibodies can be used as controls in assays designated to diagnostically or prognostically monitor polypeptide levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

The antibody conjugates of the invention can be used as a control in procedures designed to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243 56 (Alan R. Liss, Inc. 1985); Hellstrom et al., "Antibodies For Drug Delivery", in Controlled Drug Delivery (2nd Ed.), Robinson et al. (eds.), pp. 623 53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475 506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303 16 (Academic Press 1985), and Thorpe et al., "The Preparation And Cytotoxic Properties Of Antibody-Toxin Conjugates", Immunol. Rev., 62:119 58 (1982).

Example 1

Generation and Characterization of Novel Lowered Affinity Antibodies

OKT3 is a murine IgG2a antibody recognizing human CD3-ε chain, a non-variable component of T cell receptor. Binding of OKT3 antibody leading to activation of T cells initially but subsequently inducing apoptosis of the T cells. OKT3 has been used as an immunosuppressant for preventing rejection of transplanted organs (Midtvedt K, Fauchald P, Lien B, et al. (2003). "Individualized T cell monitored administration of ATG versus OKT3 in steroid-resistant kidney graft rejection". Clinical transplantation 17: 69-74). The crystal structure of OKT3 complexed with the human T cell receptor CD3-εγ heterodimer has been determined (Kjer-Nielsen L, Dunstone M A, et al. (2004) "Crystal structure of the human T cell receptor CD3 epsilon gamma heterodimer complexed to the therapeutic mAb OKT3". Proc Natl Acad Sci USA. 101:7675-7680), and provided a proof-of-concept example for engineering of the lowered affinity antibody.

The amino acid sequences of OKT3 complementarity determining regions were modified to reduce or eliminate antigen binding without affecting antibody structure or expression. Exemplary CDR sequences of lowered affinity antibodies of the invention are listed in Table 1. The resulting lowered affinity antibodies expressed normally (FIG. 3), and had minimal or no capacity to bind to human Jurkat cells (FIG. 4) or human peripheral blood mononuclear cells (PBMCs, FIG. 5) as measured by FACS plots.

TABLE 1

Exemplary lowered affinity antibody CDR sequences.

| SEQ ID NO | SEQUENCE VARIANTS | AMINO ACID CHANGES | SEQUENCE |
|---|---|---|---|
| SEQ ID NO: 1 | OKT3 CDRH1 | NA | GYTFTRYTMH |
| SEQ ID NO: 2 | CDRH1m | T33A | GYTFTRYAMH |
| SEQ ID NO: 3 | OKT3 CDRH2 | NA | YINPSRGYTNYNQKFKD |
| SEQ ID NO: 4 | CDRH2m1 | Y50A/N52A/ R55A/Y57A | AIAPSAGATNYNQKFKD |
| SEQ ID NO: 5 | CDRH2m2 | R55A | YINPSAGYTNYNQKFKD |
| SEQ ID NO: 6 | OKT3 CDRH3 | NA | YYDDHYCLDY |
| SEQ ID NO: 7 | CDRH3m1 | Y99A/ D101A/ Y104A | AYADHACLDY |
| SEQ ID NO: 8 | CDRH3m2 | D101A | YYADHYCLDY |
| SEQ ID NO: 9 | OKT3 CDRL1 | NA | SASSSVSY |
| SEQ ID NO: 10 | CDRL1m | S30A/Y31A | SASSSVAA |
| SEQ ID NO: 11 | OKT3 CDRL2 | NA | IYDTSKL |
| SEQ ID NO: 12 | CDRL2m | D49A | IYATSKL |
| SEQ ID NO: 13 | OKT3 CDRL3 | NA | QQWSSNPFT |
| SEQ ID NO: 14 | CDRL3m | W90A/S91A | QQAASNPFT |
| SEQ ID NO: 15 | FRH1 | | QVQLQQSGAELARPGAS VKMSCKAS |
| SEQ ID NO: 16 | FRH2 | | WVKQRPGQGLEWIG |
| SEQ ID NO: 17 | FRH3 | | KATLTTDKSSSTAYMQL SSLTSEDSAVYYCAR |
| SEQ ID NO: 18 | FRH4 | | WGQGTTLTVSS |
| SEQ ID NO: 19 | FRL1 | | QIVLTQSPAIMSASPGE KVTMTC |
| SEQ ID NO: 20 | FRL2 | | MNWYQQKSGTSPKRW |
| SEQ ID NO: 21 | FRL3 | | ASGVPAHFRGSGSGTSY SLTISGMEAEDAATYYC |
| SEQ ID NO: 22 | FRL4 | | FGSGTKLEIN |
| SEQ ID NO: 23 | HCVR | | QVQLQQSGAELARPGAS VKMSCKASGYTFTRYTM HWVKQRPGQGLEWIGYI |

TABLE 1-continued

Exemplary lowered affinity antibody CDR sequences.

| SEQ ID NO | SEQUENCE VARIANTS | AMINO ACID CHANGES | SEQUENCE |
|---|---|---|---|
| | | | NPSRGYTNYNQKFKDKATLTTDKSSSTAYMQLSSLTSEDSAVYYCARYYDDHYCLDYWGQGTTLTVSS |
| SEQ ID NO: 24 | LCVR | | QIVLTQSPAIMSASPGEKVTMTCSASSSVSYMNWYQQKSGTSPKRWIYDTSKLASGVPAHFRGSGSTSYSLTISGMEAEDAATYCQQWSSNPFTFGSGTKLEIN |
| SEQ ID NO: 25 | CDRH1m | T33A | QVQLQQSGAELARPGASVKMSCKASGYTFTRYAMHWVKQRPGQGLEWIGYINPSRGYTNYNQKFKDKATLTTDKSSSTAYMQLSSLTSEDSAVYYCARYYDDHYCLDYWGQGTTLTVSS |
| SEQ ID NO: 26 | CDRH2m1 | Y50A/N52A/R55A/Y57A | QVQLQQSGAELARPGASVKMSCKASGYTFTRYTMHWVKQRPGQGLEWIGAIAPSAGATNYNQKFKDKATLTTDKSSSTAYMQLSSLTSEDSAVYYCARYYDDHYCLDYWGQGTTLTVSS |
| SEQ ID NO: 27 | CDRH2m2 | R55A | QVQLQQSGAELARPGASVKMSCKASGYTFTRYTMHWVKQRPGQGLEWIGYINPSAGYTNYNQKFKDKATLTTDKSSSTAYMQLSSLTSEDSAVYYCARYYDDHYCLDYWGQGTTLTVSS |
| SEQ ID NO: 28 | CDRH3m1 | Y99A/D101A/Y104A | QVQLQQSGAELARPGASVKMSCKASGYTFTRYTMHWVKQRPGQGLEWIGYINPSRGYTNYNQKFKDKATLTTDKSSSTAYMQLSSLTSEDSAVYYCARAYADHACLDYWGQGTTLTVSS |
| SEQ ID NO: 29 | CDRH3m2 | D101A | QVQLQQSGAELARPGASVKMSCKASGYTFTRYTMHWVKQRPGQGLEWIGYINPSRGYTNYNQKFKDKATLTTDKSSSTAYMQLSSLTSEDSAVYYCARYYADHYCLDYWGQGTTLTVSS |
| SEQ ID NO: 30 | CDRH1m CDRH2m1 | T33A; Y50A/N52A/R55A/Y57A | QVQLQQSGAELARPGASVKMSCKASGYTFTRYAMHWVKQRPGQGLEWIGAIAPSAGATNYNQKFKDKATLTTDKSSSTAYMQLSSLTSEDSAVYYCARYYDDHYCLDYWGQGTTLTVSS |
| SEQ ID NO: 31 | CDRH1m CDRH2m2 | T33A; R55A | QVQLQQSGAELARPGASVKMSCKASGYTFTRYAMHWVKQRPGQGLEWIGYINPSAGYTNYNQKFKDKATLTTDKSSSTAYMQLSSLTSEDSAVYYCARYYDDHYCLDYWGQGTTLTVSS |
| SEQ ID NO: 32 | CDRH1m CDRH3m1 | T33A; Y99A/D101A/Y104A | QVQLQQSGAELARPGASVKMSCKASGYTFTRYAMHWVKQRPGQGLEWIGYINPSRGYTNYNQKFKDKATLTTDKSSSTAYMQLSS |

TABLE 1-continued

Exemplary lowered affinity antibody CDR sequences.

| SEQ ID NO | SEQUENCE VARIANTS | | | AMINO ACID CHANGES | SEQUENCE |
|---|---|---|---|---|---|
| | | | | | LTSEDSAVYYCARYYDD HYCLDYWGQGTTLTVSS |
| SEQ ID NO: 33 | CDRH1m | CDRH3m2 | | T33A; D101A | QVQLQQSGAELARPGAS VKMSCKASGYTFTRYAM HWVKQRPGQGLEWIGYI NPSRGYTNYNQKFKDKA TLTTDKSSSTAYMQLSS LTSEDSAVYYCARYYDD HYCLDYWGQGTTLTVSS |
| SEQ ID NO: 34 | CDRH2m1 | CDRH3m1 | | Y50A/N52A/ R55A/Y57A; Y99A/ D101A/ Y104A | QVQLQQSGAELARPGAS VKMSCKASGYTFTRYTM HWVKQRPGQGLEWIGYI NPSRGYTNYNQKFKDKA TLTTDKSSSTAYMQLSS LTSEDSAVYYCARAYAD HACLDYWGQGTTLTVSS |
| SEQ ID NO: 35 | CDRH2m1 | CDRH3m2 | | Y50A/N52A/ R55A/Y57A; D101A | QVQLQQSGAELARPGAS VKMSCKASGYTFTRYTM HWVKQRPGQGLEWIGYI NPSRGYTNYNQKFKDKA TLTTDKSSSTAYMQLSS LTSEDSAVYYCARYYDD HYCLDYWGQGTTLTVSS |
| SEQ ID NO: 36 | CDRH2m2 | CDRH3m1 | | R55A; Y99A/ D101A/ Y104A | QVQLQQSGAELARPGAS VKMSCKASGYTFTRYTM HWVKQRPGQGLEWIGYI NPSRGYTNYNQKFKDKA TLTTDKSSSTAYMQLSS LTSEDSAVYYCARYYDD HYCLDYWGQGTTLTVSS |
| SEQ ID NO: 37 | CDRH2m2 | CDRH3m2 | | R55A; D101A | QVQLQQSGAELARPGAS VKMSCKASGYTFTRYTM HWVKQRPGQGLEWIGYI NPSRGYTNYNQKFKDKA TLTTDKSSSTAYMQLSS LTSEDSAVYYCARYYAD HYCLDYWGQGTTLTVSS |
| SEQ ID NO: 38 | CDRH1m | CDRH2m1 | CDRH3m1 | T33A; Y50A/N52A/ R55A/Y57A; Y99A/ D101A/ Y104A | QVQLQQSGAELARPGAS VKMSCKASGYTFTRYAM HWVKQRPGQGLEWIGAI APSAGATNYNQKFKDKA TLTTDKSSSTAYMQLSS LTSEDSAVYYCARAYAD HACLDYWGQGTTLTVSS |
| SEQ ID NO: 39 | CDRH1m | CDRH2m2 | CDRH3m1 | T33A; Y50A/N52A/ R55A/Y57A; D101A | QVQLQQSGAELARPGAS VKMSCKASGYTFTRYAM HWVKQRPGQGLEWIGYI NPSAGYTNYNQKFKDKA TLTTDKSSSTAYMQLSS LTSEDSAVYYCARAYAD HACLDYWGQGTTLTVSS |
| SEQ ID NO: 40 | CDRH1m | CDRH2m1 | CDRH3m2 | T33A; R55A; Y99A/ D101A/ Y104A | QVQLQQSGAELARPGAS VKMSCKASGYTFTRYAM HWVKQRPGQGLEWIGAI APSAGATNYNQKFKDKA TLTTDKSSSTAYMQLSS LTSEDSAVYYCARYYAD HYCLDYWGQGTTLTVSS |
| SEQ ID NO: 41 | CDRH1m | CDRH2m2 | CDRH3m2 | T33A; R55A; D101A | QVQLQQSGAELARPGAS VKMSCKASGYTFTRYAM HWVKQRPGQGLEWIGYI NPSAGYTNYNQKFKDKA TLTTDKSSSTAYMQLSS LTSEDSAVYYCARYYAD HYCLDYWGQGTTLTVSS |

TABLE 1-continued

Exemplary lowered affinity antibody CDR sequences.

| SEQ ID NO | SEQUENCE VARIANTS | | | AMINO ACID CHANGES | SEQUENCE |
|---|---|---|---|---|---|
| SEQ ID NO: 42 | CDRL1m | | | S30A/Y31A | QIVLTQSPAIMSASPGE KVTMTCSASSSVAAMNW YQQKSGTSPKRWIYDTS KLASGVPAHFRGSGSGT SYSLTISGMEAEDAATY YCQQWSSNPFTFGSGTK LEIN |
| SEQ ID NO: 43 | CDRL2m | | | D49A | QIVLTQSPAIMSASPGE KVTMTCSASSSVSYMNW YQQKSGTSPKRWIYATS KLASGVPAHFRGSGSGT SYSLTISGMEAEDAATY YCQQWSSNPFTFGSGTK LEIN |
| SEQ ID NO: 44 | CDRL3m | | | W90A/S91A | QIVLTQSPAIMSASPGE KVTMTCSASSSVSYMNW YQQKSGTSPKRWIYDTS KLASGVPAHFRGSGSGT SYSLTISGMEAEDAATY YCQQAASNPFTFGSGTK LEIN |
| SEQ ID NO: 45 | CDRL1m | CDRL2m | | S30A/Y31A; D49A | QIVLTQSPAIMSASPGE KVTMTCSASSSVAAMNW YQQKSGTSPKRWIYATS KLASGVPAHFRGSGSGT SYSLTISGMEAEDAATY YCQQWSSNPFTFGSGTK LEIN |
| SEQ ID NO: 46 | CDRL1m | CDRL3m | | S30A/Y31A; W90A/S91A | QIVLTQSPAIMSASPGE KVTMTCSASSSVAAMNW YQQKSGTSPKRWIYDTS KLASGVPAHFRGSGSGT SYSLTISGMEAEDAATY YCQQAASNPFTFGSGTK LEIN |
| SEQ ID NO: 47 | CDRL2m | CDRL3m | | D49A; W90A/S91A | QIVLTQSPAIMSASPGE KVTMTCSASSSVSYMNW YQQKSGTSPKRWIYATS KLASGVPAHFRGSGSGT SYSLTISGMEAEDAATY YCQQAASNPFTFGSGTK LEIN |
| SEQ ID NO: 48 | CDRL1m | CDRL2m | CDRL3m | S30A/Y31A; D49A; W90A/S91A | QIVLTQSPAIMSASPGE KVTMTCSASSSVAAMNW YQQKSGTSPKRWIYATS KLASGVPAHFRGSGSGT SYSLTISGMEAEDAATY YCQQAASNPFTTFGSGT KLEIN |

Cell Lines and Media

Human 293T cells were maintained in Dulbecco's Modified Eagles's medium (DMEM) supplemented with 10% fetal bovine serum (FBS) (Invitogen, Gibco, Carlsbad, Calif.), 2 mM L-glutamine, and 40 ug/ml of gentamicin. Mouse OKT3, an anti-human CD3 antibody producing hybridoma cell line, was grown in Iscove's Modified Dulbecco's medium (IMDM) containing 10% FBS, 1 mM sodium pyruvate, 2 mM L-glutamine, and 40 ug/ml of gentamicin. Jurkat E6.1, a human leukemic T cell line, was grown in RPMI medium supplemented with 10% FBS, 2 mM L-glutamine, and 40 ug/ml of gentamicin. All media and supplements were purchased from Lonza, Walkville, Md., except for FBS.

Construction of OKT3 Heavy and Light Chain Expression Plasmids

Total RNA was isolated from OKT3 hybridoma cell line using TRIzol Reagent from Invitrogen. cDNA was synthesized using SuperScript™ III Reverse Transcriptase (Invitrogen) and Oligo (dT)12-18 Primer (SEQ ID NO: 49) (Invitrogen).

Based on Genbank records of mouse OKT3 heavy chain (Accession #A22261) and light chain (Accession #A22259) nucleotide sequences, the entire coding sequences of the heavy and light chains were amplified via polymerase chain reactions (PCR) with oligo dT-primed cDNA of OKT3 hybridoma as the template, and cloned into a mammalian expression plasmid, driven by CMV Immediate Early gene promoter, called pME. The complete amino acid sequence of the mouse OKT3 heavy chain encoded from plasmid pME-wtOKT3 HC (FIG. 6) is represented in SEQ ID NO: 23 and the complete amino acid sequence of the mouse OKT3 light chain encoded from plasmid pME-wtOKT3LC (FIG. 7) is represented in SEQ ID NO: 24.

Construction of Expression Plasmids Encoding OKT3 Heavy and Light Chain Variants Site directed mutagenesis was performed using standard PCR techniques to generate the OKT3 heavy and light chain variants, replacing various antigen contacting amino acids within the CDRs with alanine. PCR fragments harboring the mutations were cloned into the same expression plasmid pME. The resultant plasmids were confirmed by sequencing reactions.

Transfection

The OKT3 and variant antibodies were produced by transient transfection using the standard calcium phosphate method. Briefly, 293T cells were seeded in 6-well plates at $6 \times 10^5$ cells/3 ml 293T medium/well 20-24 hours before transfection. 3 hours prior to transfection, the culture medium was changed to IMDM supplemented with 10% FBS, 25 mM Hepes buffer and 40 ug/ml gentamycin. The transfection procedure was carried out by first mixing 8 µg each of the OKT3 heavy and light chain plasmid DNAs with 31 µl of 2M $CaCl_2$ and sterile distilled water for a final volume of 250 µl. The DNA/calcium mixture was then slowly added to 250 µl of 2×HBS buffer (281 mM NaCl, 100 mM HEPES, 1.5 mM $Na_2HPO4$ at pH 7.12). The transfection mixture was incubated at room temperature for 20 minutes, and then added slowly to the 293T cultures. 12-16 hours after transfection, the culture medium was changed once again to the complete 293T medium. 40-48 hours after transfection, culture supernatants containing OKT3 variant antibodies were harvested, and used for subsequent analyses.

Antibody Quantitation

The amount of OKT3 and variant antibodies produced by transient transfection was determined by the Guava RapidQuant mouse IgG Kit (Guava Technologies, Hayward, Calif.) following the manufacture's protocol. In brief, 10 µl of supernatant from each transfection was incubated with IgG capture beads for 40 min with shaking. Subsequently, FITC-conjugated goat anti-mouse IgG was added to each sample and incubated 60 minutes with shaking. The sample volume was brought up to 200 µl and run on Guava EasyCyte system (Guava). The antibody concentration in each sample was calculated by comparing the mean florescence channel (MFI) of the samples with those of the standards.

Isolation of Human Peripheral Mononuclear Cells (hPBMC)

Human peripheral mononuclear cells (hPBMC) were isolated using Ficoll-paque gradient method. In brief, human whole blood was diluted 1:1 with 1× Phosphate Buffered Saline (PBS) and carefully layered on the top of Ficoll-paque (0.4 volume of blood sample volume) (GE Healthcare, Uppsala, Sweden). After centrifugation at 900 g for 30 min, hPBMC at the interface of blood and Ficoll-paque were carefully extracted. Cell suspensions were diluted 1:3 with 1×PBS and spun at 400 g for 10 min at 8-20° C. Cell pellets were washed one more time with 1×PBS at 400 g for 10 min at 8-20° C. and diluted with FACS buffer (PBS with 2% FCS, 0.1% $NaN_3$) for flow cytometric analysis.

Flow Cytometry

Human Jurkat cells ($1 \times 10^5$ cells/well in 96-well plates) or hPBMC ($3 \times 10^5$ cells/well in 96-well plates) were incubated with 100 µl of transfection supernatant of OKT3 or its variants at 4° C. for 60 minute and washed twice with 200 µl of FACS buffer. Cells were stained with 100 µl of phycoerythrin (PE)-conjugated goat-anti-mouse Immunoglobulin G (Invitrogen-Caltag, Carlsbad, Calif.) for 60 min at 4° C., and washed twice with 200 µl of FACS buffer. The cells were then fixed with 1% paraformaldehyde for 15 minute at 4° C., and washed once with FACS buffer. Cells were then resuspended in 200 µl of FACS buffer for analysis on a Guava EaseCyte Plus system (Guava Technologies, Inc., Hayward, Calif.).

Binding of OKT3 and OKT3 Variant to Jurkat Cells.

Figure 8:
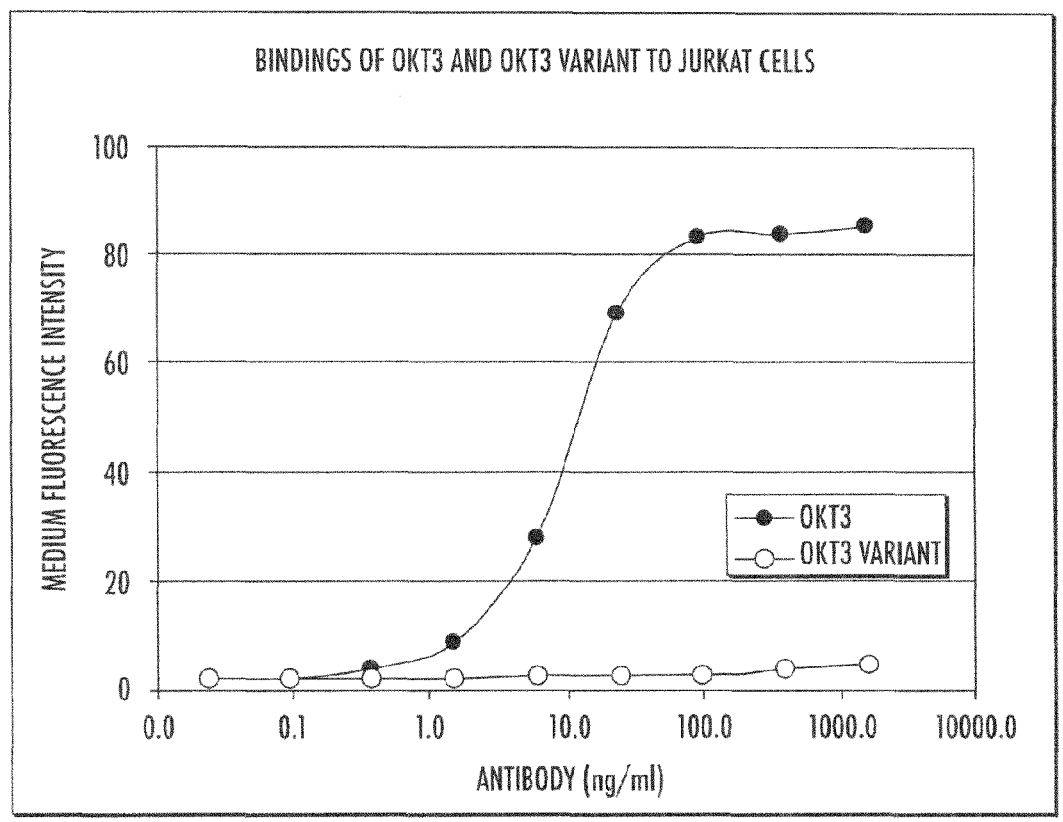
FIG. 8 shows the binding of OKT3 and OKT3 variant to Jurkat cells.

A total of $1 \times 10^5$ Jurket cells were incubated with serially diluted OKT3 or OKT3 variant antibody, followed with PE-conjugated goat anti-mouse IgG, and analyzed by the FACS. At 1600 ng/ml, binding of OKT3 variant is comparable to that of OKT3 antibody at 0.4 ng/ml. Thus, the binding affinity of OKT3 variant is approximately 4000× less than that of the parental OKT3 antibody (FIG. 8).

Pharmacokinetics of the Variant Antibody.

Figure 9:
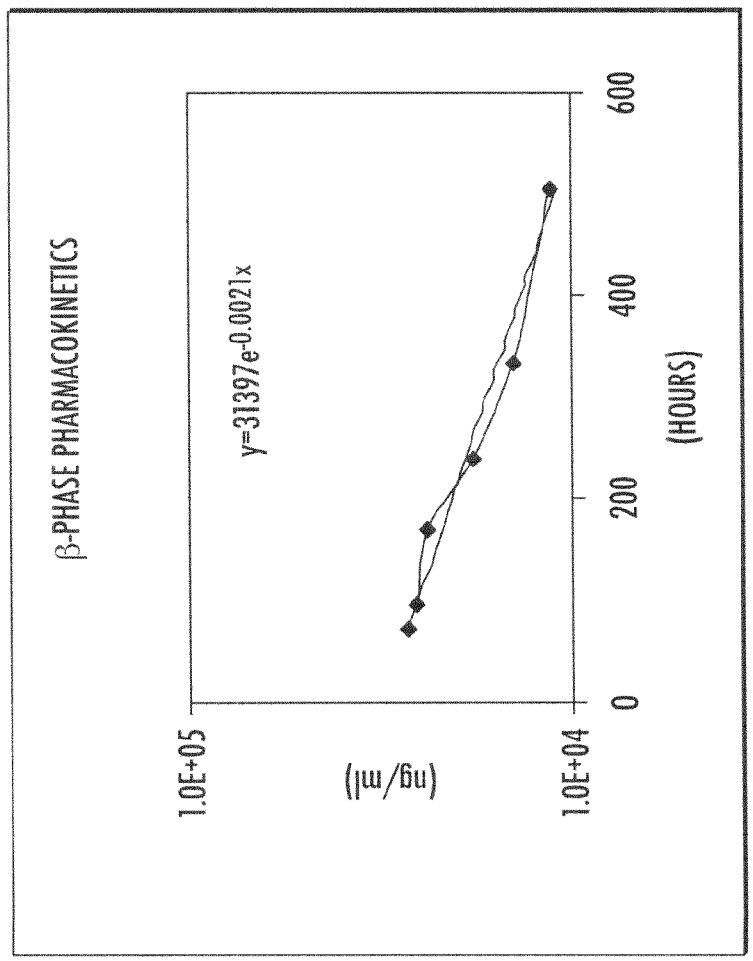
FIG. 9 shows a pharmacokinetics of the variant antibody.

Pharmacokinetic analysis of the variant IgG2a antibody. An IgG2a antibody was produced by co-expressing of a CDR mutated heavy chain (Seq No. 26) and a CDR mutated light chain (Seq No. 47). While it is clear that this variant antibody no longer binds to the CD3 which is the antigen of the parental antibody, OKT3, it is not known whether this antibody may serendipitously interact yet with another antigen(s). One way to test this is to determine if the variant antibody has an in vivo half life similar to endogenous circulating IgG2a antibody. The variant antibody was administered in B6 mice and serum samples were collected up to 21 days. The concentration of recombinant IgG2a antibody was measured by an allotype specific anti-mouse antibody. The half life of the antibody was calculated by fitting the beta-phase of the pharmacokinetic profile and determined to be 13.75 days (FIG. 9). This half life is close agreement with the reported 10-15 days half of murine IgG2a antibody (Talbotp, P. J. and Buchmeie M. J. Catabolism of homologous murine monoclonal hybridoma IgG antibodies in mice. Immunology 60:485-489, 1987). The long serum half life indicates that this antibody is likely not interacting with an unexpected antigen(s) and is not discriminated from the endogenous immunoglobulins.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated modified OKT3 antibody or antigen binding fragment thereof comprising:
   a light chain comprising:
   a light chain Complementary Determining Region (L-CDR)1, a L-CDR2, and a L-CDR3, wherein L-CDR1, L-CDR2 and L-CDR3 are parental OKT3 antibody L-CDR1, L-CDR2 and L-CDR3, respectively; and
   a heavy chain comprising:
   a heavy chain Complementary Determining Region (H-CDR)1, a H-CDR2, and a H-CDR3, wherein
   i) H-CDR1 has the amino acid sequence set forth as SEQ ID NO.: 2, and H-CDR2 and H-CDR3 are parental OKT3 antibody H-CDR2 and H-CDR3, respectively, or
   ii) H-CDR2 has the amino acid sequence set forth as SEQ ID NO.: 4, and H-CDR1 and H-CDR3 are parental OKT3 antibody H-CDR1 and H-CDR3, respectively, or
   iii) H-CDR2 has the amino acid sequence set forth as SEQ ID NO.: 5, and H-CDR1 and H-CDR3 are parental OKT3 antibody H-CDR1 and H-CDR3, respectively, or
   iv) H-CDR3 has the amino acid sequence set forth as SEQ ID NO.: 7, and H-CDR1 and H-CDR2 are parental OKT3 antibody H-CDR1 and H-CDR2, respectively, or
   v) H-CDR3 has the amino acid sequence set forth as SEQ ID NO.: 8, and H-CDR1 and H-CDR2 are parental OKT3 antibody H-CDR1 and H-CDR2, respectively,
   and wherein the entire framework region of the modified OKT3 antibody or antigen binding fragment thereof is identical to that of parental OKT3 antibody.

2. An isolated modified OKT3 antibody or antigen binding fragment thereof comprising:
   a light chain comprising:
   a light chain Complementary Determining Region (L-CDR)1, a L-CDR2, and a L-CDR3, wherein L-CDR2 and L-CDR3 are parental OKT3 antibody L-CDR2 and L-CDR3, respectively, and wherein L-CDR1 has the amino acid sequence set forth as SEQ ID NO.: 10; and
   a heavy chain comprising:
   a heavy chain Complementary Determining Region (H-CDR)1, a H-CDR2, and a H-CDR3, wherein
   i) H-CDR1 has the amino acid sequence set forth as SEQ ID NO.: 2, and H-CDR2 and H-CDR3 are parental OKT3 antibody H-CDR2 and H-CDR3, respectively, or
   ii) H-CDR2 has the amino acid sequence set forth as SEQ ID NO.: 4, and H-CDR1 and H-CDR3 are parental OKT3 antibody H-CDR1 and H-CDR3, respectively, or
   iii) H-CDR2 has the amino acid sequence set forth as SEQ ID NO.: 5, and H-CDR1 and H-CDR3 are parental OKT3 antibody H-CDR1 and H-CDR3, respectively, or
   iv) H-CDR3 has the amino acid sequence set forth as SEQ ID NO.: 7, and H-CDR1 and H-CDR2 are parental OKT3 antibody H-CDR1 and H-CDR2, respectively, or
   v) H-CDR3 has the amino acid sequence set forth as SEQ ID NO.: 8, and H-CDR1 and H-CDR2 are parental OKT3 antibody H-CDR1 and H-CDR2, respectively, or
   vi) H-CDR1, H-CDR2 and H-CDR3 are parental OKT3 antibody H-CDR1, H-CDR2 and H-CDR3, respectively, and wherein the entire framework region of the modified OKT3 antibody or antigen binding fragment thereof is identical to that of parental OKT3 antibody.

3. An isolated modified OKT3 antibody or antigen binding fragment thereof comprising:
   a light chain comprising:
      a light chain Complementary Determining Region (L-CDR)1, a L-CDR2, and a L-CDR3, wherein L-CDR1 and L-CDR3, are parental OKT3 antibody L-CDR1 and L-CDR3, respectively, and wherein L-CDR2 has the amino acid sequence set forth as SEQ ID NO.: 12; and
   a heavy chain comprising:
      a heavy chain Complementary Determining Region (H-CDR)1, a H-CDR2, and a H-CDR3, wherein
         i) H-CDR1 has the amino acid sequence set forth as SEQ ID NO.: 2, and H-CDR2 and H-CDR3 are parental OKT3 antibody H-CDR2 and H-CDR3, respectively, or
         ii) H-CDR2 has the amino acid sequence set forth as SEQ ID NO.: 4, and H-CDR1 and H-CDR3 are parental OKT3 antibody H-CDR1 and H-CDR3, respectively, or
         iii) H-CDR2 has the amino acid sequence set forth as SEQ ID NO.: 5, and H-CDR1 and H-CDR3 are parental OKT3 antibody H-CDR1 and H-CDR3, respectively, or
         iv) H-CDR3 has the amino acid sequence set forth as SEQ ID NO.: 7, and H-CDR1 and H-CDR2 are parental OKT3 antibody H-CDR1 and H-CDR2, respectively, or
         v) H-CDR3 has the amino acid sequence set forth as SEQ ID NO.: 8, and H-CDR1 and H-CDR2 are parental OKT3 antibody H-CDR1 and H-CDR2, respectively, or
         vi) H-CDR1, H-CDR2 and H-CDR3 are parental OKT3 antibody H-CDR1, H-CDR2 and H-CDR3, respectively,
   and wherein the entire framework region of the modified OKT3 antibody or antigen binding fragment thereof is identical to that of parental OKT3 antibody.

4. An isolated modified OKT3 antibody or antigen binding fragment thereof comprising:
   a light chain comprising:
      a light chain Complementary Determining Region (L-CDR)1, a L-CDR2, and a L-CDR3, wherein L-CDR1 and L-CDR2, are parental OKT3 antibody L-CDR1 and L-CDR2, respectively, and wherein L-CDR3 has the amino acid sequence set forth as SEQ ID NO.: 14; and
   a heavy chain comprising:
      a heavy chain Complementary Determining Region (H-CDR)1, a H-CDR2, and a H-CDR3, wherein
         i) H-CDR1 has the amino acid sequence set forth as SEQ ID NO.: 2, and H-CDR2 and H-CDR3 are parental OKT3 antibody H-CDR2 and H-CDR3, respectively, or
         ii) H-CDR2 has the amino acid sequence set forth as SEQ ID NO.: 4, and H-CDR1 and H-CDR3 are parental OKT3 antibody H-CDR1 and H-CDR3, respectively, or
         iii) H-CDR2 has the amino acid sequence set forth as SEQ ID NO.: 5, and H-CDR1 and H-CDR3 are parental OKT3 antibody H-CDR1 and H-CDR3, respectively, or
         iv) H-CDR3 has the amino acid sequence set forth as SEQ ID NO.: 7, and H-CDR1 and H-CDR2 are parental OKT3 antibody H-CDR1 and H-CDR2, respectively, or
         v) H-CDR3 has the amino acid sequence set forth as SEQ ID NO.: 8, and H-CDR1 and H-CDR2 are parental OKT3 antibody H-CDR1 and H-CDR2, respectively, or
         vi) H-CDR1, H-CDR2 and H-CDR3 are parental OKT3 antibody H-CDR1, H-CDR2 and H-CDR3, respectively,
   and wherein the entire framework region of the modified OKT3 antibody or antigen binding fragment thereof is identical to that of parental OKT3 antibody.

* * * * *

UNITED STATES PATENT AND TRADEMARK OFFICE
CERTIFICATE OF CORRECTION

PATENT NO.        : 8,530,629 B2                                          Page 1 of 2
APPLICATION NO.   : 13/146805
DATED             : September 10, 2013
INVENTOR(S)       : Hsiu-Ching Chang It is certified that error appears in the above-identified patent and that said Letters Patent is hereby corrected as shown below:

In the Drawings

Figure 4:
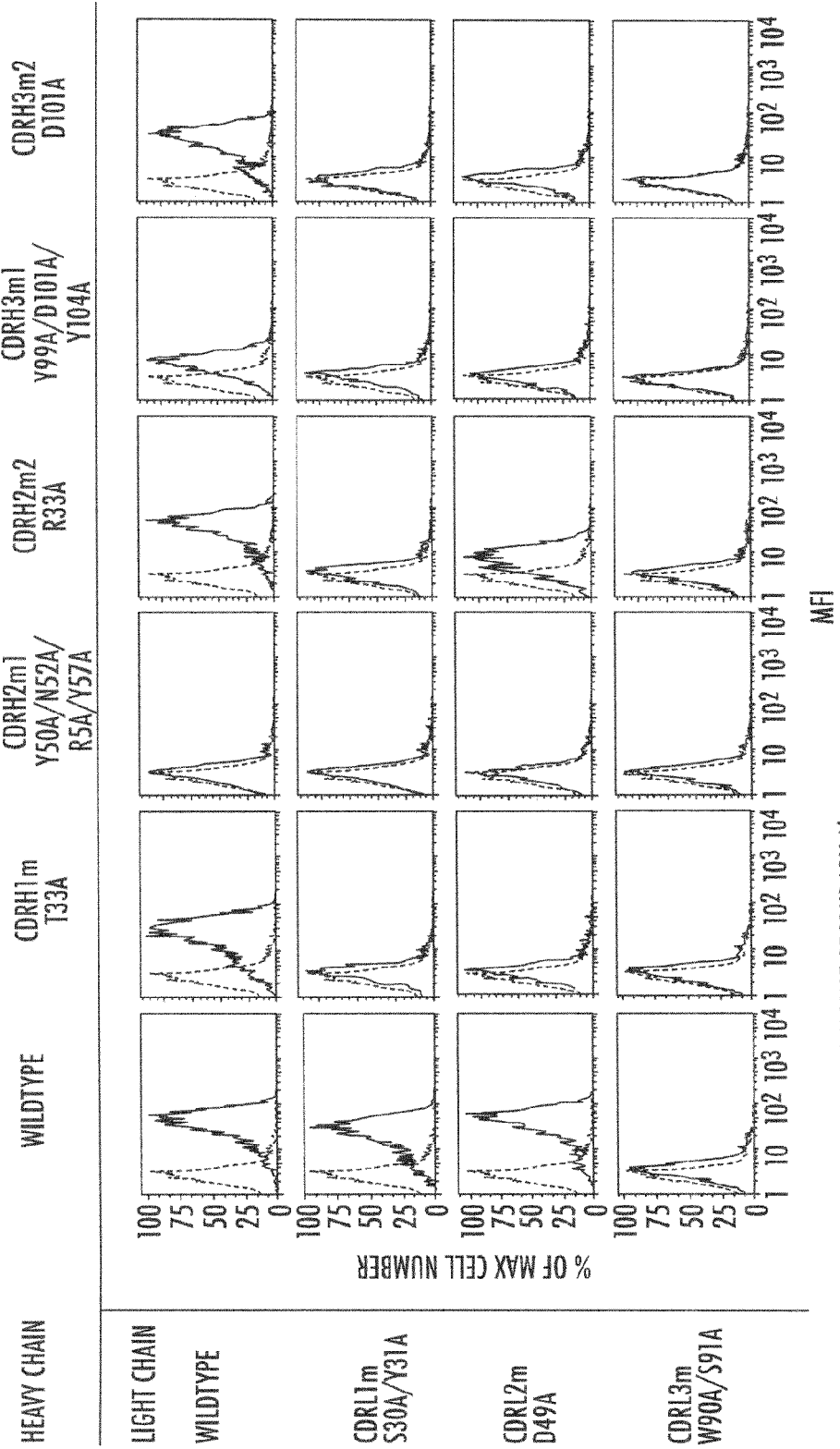
FIG. 4 shows FACS plots demonstrating reduced binding of some exemplary lowered affinity antibodies of the invention to human Jurkat cells, which express CD3.

In Figure 4, top row, replace "CDRH2m1
                               Y50A/N52A/
                               R5A/Y57A"
with
                            -- CDRH2m1
                               Y50A/N52A/
                               R55A/Y57A --

In Figure 4, top row, replace "CDRH2m2
                               R33A"
with
                            -- CDRH2m2
                               R55A --

Figure 5:
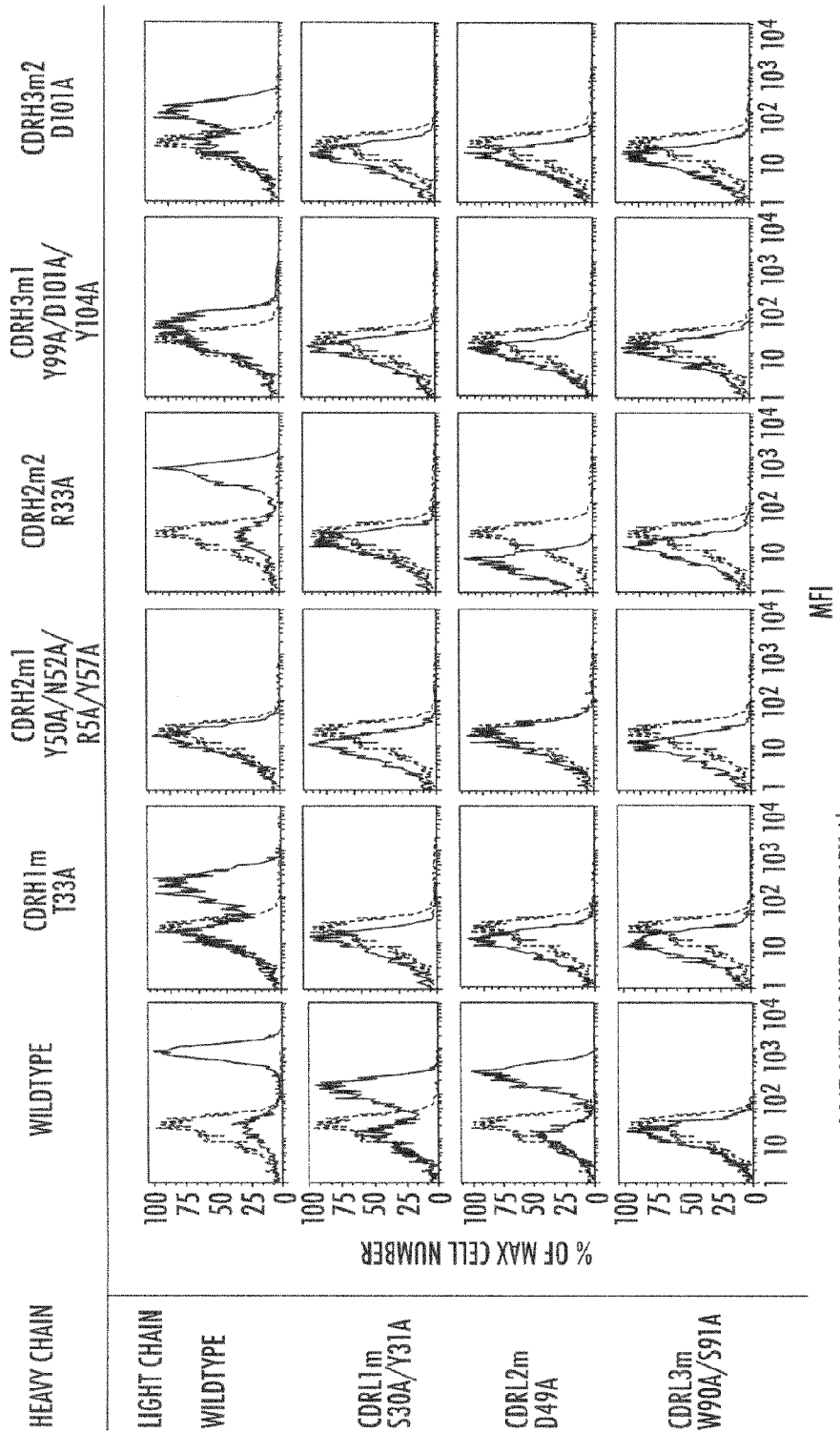
FIG. 5 shows FACS plots demonstrating reduced binding of some exemplary lowered affinity antibodies of the invention to human PBMC, which contain CD3 expressing cells.
Figure 6:
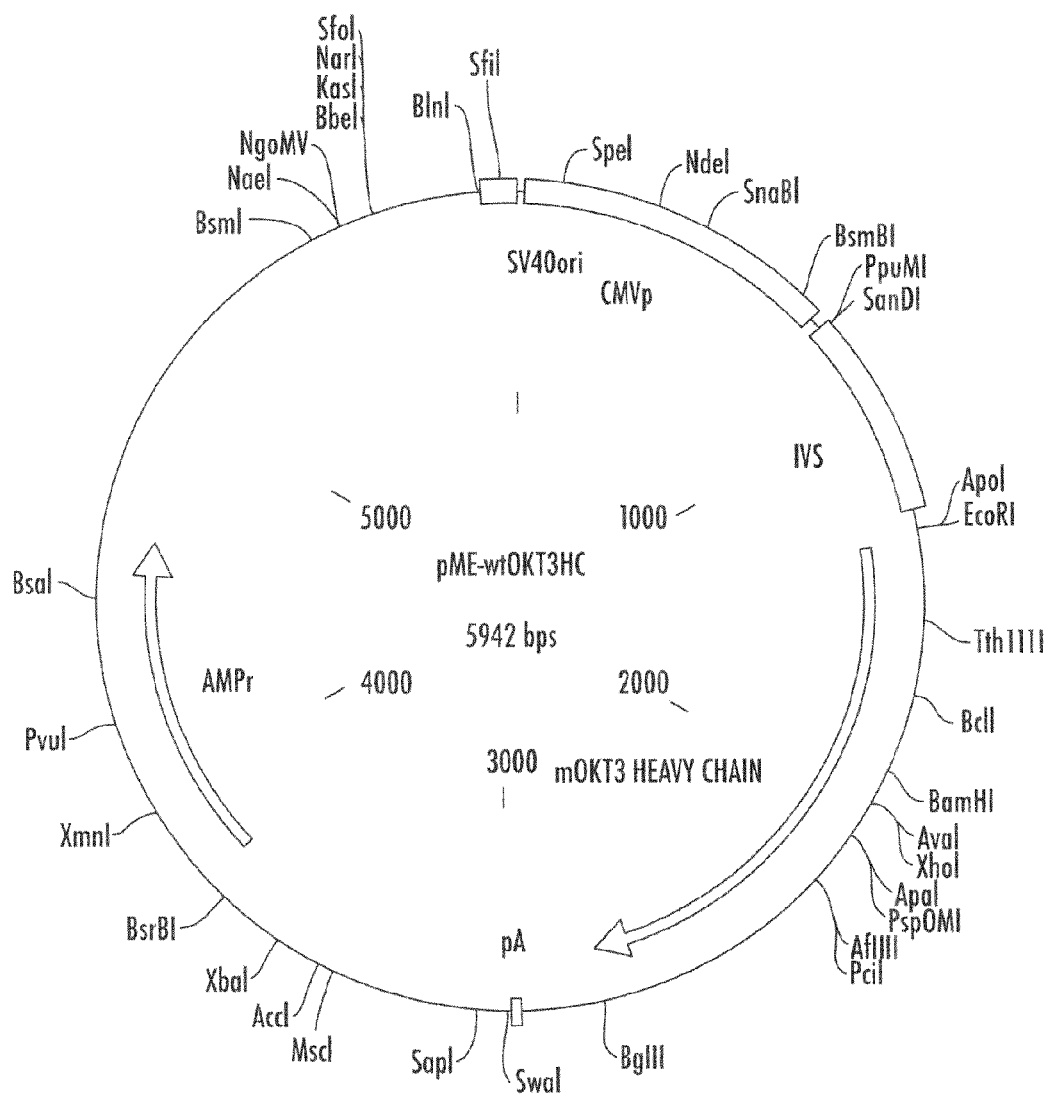
FIG. 6 shows a map of the pME-wtOKT3 HC vector that encodes the OKT3 heavy chain.

In Figure 5, top row, replace "CDRH2m1
                               Y50A/N52A/
                               R5A/Y57A"
with
                            -- CDRH2m1
                               Y50A/N52A/
                               R55A/Y57A --

In Figure 5, top row, replace "CDRH2m2
                               R33A"
with
                            -- CDRH2m2
                               R55A --

Signed and Sealed this
Eleventh Day of February, 2014

Michelle K. Lee
*Deputy Director of the United States Patent and Trademark Office*

Figure 7:
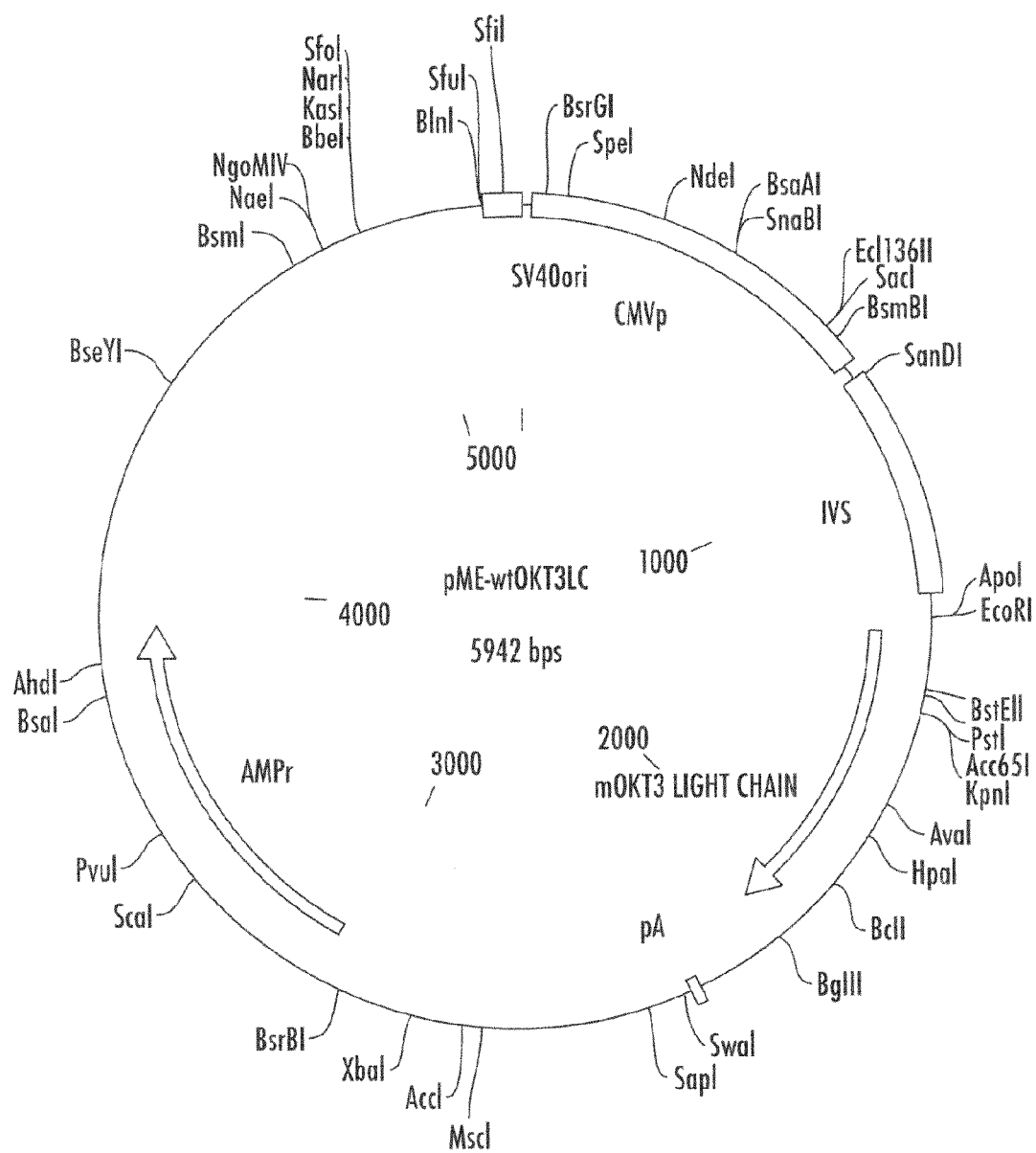
FIG. 7 shows a map of the pME-wtOKT3 LC vector that encodes the OKT3 light chain.

In Figure 7, center, replace "5942bps" with -- 5242bps --

In Figure 9, title, replace "PHARMACOKINETICS OF OKT3-NC [SEQ 26X47] IN C57B6 MICE" with -- PHARMACOKINETICS OF OKT3 VARIANT IN C57B6 MICE --

In the Specification

At Column 28, Line 23, replace "(Seq No 47)" with -- (Seq No 44) --